United States Patent [19]
Hermecz et al.

[11] Patent Number: 4,461,769
[45] Date of Patent: Jul. 24, 1984

[54] NITROGEN BRIDGEHEAD COMPOUNDS HAVING ANTI-ALLERGIC EFFECT

[75] Inventors: Istvan Hermecz; Zoltan Meszarós; Tibor Breining; Sandor Virag; Lelle Vasvari nèe Debreczy; Ägnes Horvàth; Gabor Nagy; Attila Mandi; Tamas Szucs; Istvan Bitter; Gyula Sebestyen, all of Budapest, Hungary

[73] Assignee: Chinoin Gyogyszer es Vegyeszeti Termekek Gyara R.T., Budapest, Hungary

[21] Appl. No.: 76,811

[22] Filed: Sep. 19, 1979

Related U.S. Application Data

[63] Continuation-in-part of Ser. No. 967,958, Dec. 11, 1978.

[30] Foreign Application Priority Data

Dec. 29, 1977 [HU] Hungary ............................ CI 1794

[51] Int. Cl.³ .................. A61K 31/505; C07D 471/04
[52] U.S. Cl. ...................................... 424/251; 544/282
[58] Field of Search ............... 544/282, 252, 116, 119; 542/418, 419, 432, 458; 424/251, 248.53, 248.56

[56] References Cited

U.S. PATENT DOCUMENTS

| 2,786,056 | 3/1957 | Sletzinger et al. | 544/422 X |
| 2,894,031 | 7/1959 | Rudner | 260/566 B |
| 3,140,315 | 7/1964 | Klös et al. | 260/566 B |
| 3,141,043 | 7/1964 | McBee | 260/566 B |
| 3,153,031 | 10/1964 | Alicot et al. | 260/566 B X |
| 3,417,082 | 12/1968 | Taylor | 542/419 |
| 3,534,100 | 10/1970 | Bollag et al. | 260/569 |
| 3,585,198 | 6/1971 | Meszaros et al. | 544/282 |
| 4,024,132 | 5/1977 | L'Eplattenier et al. | 542/419 X |
| 4,123,533 | 10/1978 | Hermecz et al. | 424/251 |

FOREIGN PATENT DOCUMENTS 873194 4/1979 Belgium .

OTHER PUBLICATIONS

Migrdichian, "Organic Synthesis", vol, 2, Reinhold Publishing Co., New York, (1957), pp. 1519-1521.
Noller, "Chemistry of Organic Compounds", 3rd ed., W. B. Saunders Co., Philadelphia, (1965), pp. 253-254, 516-517, 597, 676.
Macarovici, et al., Chemical Abstracts, vol. 61, 9371h, (1964).

Primary Examiner—Donald G. Daus
Assistant Examiner—Diana G. Rivers
Attorney, Agent, or Firm—Karl F. Ross; Herbert Dubno

[57] ABSTRACT

Compounds of the formula I

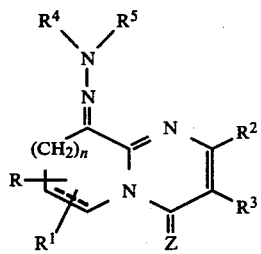

or pharmaceutically acceptable salts, hydrates, stereo-isomers, optically active isomers, geometrical isomers or tautomeric forms thereof are disclosed wherein
  R is hydrogen or lower alkyl
  $R^1$ is hydrogen, lower alkyl, styryl, or a carboxylic acid; or
  R and $R^1$ together form a group of the formula —(CH=CH)$_2$— and in this case the broken line represents a further C—C bond, while in all other cases there is a single bond between positions 6 and 7;
  $R^2$ is hydrogen, lower alkyl or hydroxy;
  $R^3$ is hydrogen, lower alkyl, aryl, lower alkanoyl, carboxyl or a carboxyl acid derivative or a group of the formula —(CH$_2$)m—COOH or a derivative thereof formed in the carboxylic group;
  n=1–3;
  $R^4$ is hydrogen, lower alkyl which can be substituted by hydroxy or carboxy; trifluoromethyl, substituted or unsubstituted aryl, phenyl-lower alkyl or substituted or an unsubstituted heterocyclic group;
  $R^5$ is hydrogen, lower alkanoyl, substituted or unsubstituted benzoyl or heteroaryl; or
  $R^4$ and $R^5$ together with the adjacent nitrogen atom form a piperidino, pyrrolidino or morpholino ring; or
  $R^4$ and $R^5$ together with the adjacent nitrogen atom form a group of the formula

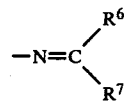

wherein $R^6$ is hydrogen and $R^7$ is substituted or unsubstituted phenyl; and
Z is oxygen. The new compounds are useful for treating asthma.

23 Claims, No Drawings

NITROGEN BRIDGEHEAD COMPOUNDS HAVING ANTI-ALLERGIC EFFECT

CROSS REFERENCE TO RELATED APPLICATIONS

This application is a continuation-in-part of copending U.S. application Ser. No. 967,958 filed Dec. 11, 1978 and claiming a Hungarian priority date of Dec. 29, 1977.

This invention relates to new nitrogen bridgehead condensed pyrimidine derivatives and to a process for their preparation. These new compounds can be used in therapy as anti-allergic and anti-asthamatic agents. Our invention also relates to pharmaceutical compositions containing these compounds.

It is known that pyrido(1,2-a)pyrimidine derivatives possess valuable analgesic and other central nervous system properties (British Pat. No. 1,209,946). One of the most preferred of these compounds for clinical practice as an analgesic is the 1,6-dimethyl-3-ethoxy-carbonyl-4-oxo-4H-pyrido(1,2-a)-pyrimidinium-metho-sulfate. (PROBON®, Rimazolium) [Arzneimittelforschung 22,815 (1972)]. Pyrido(1,2-a)pyrimidine derivatives may be prepared by cyclization of the corresponding dialkyl-(2-pyridyl-amino-methylene)-malonate. Other substituted pyrido(1,2-a)pyrimidine derivatives are described in British Pat. No. 1,454,312.

This application discloses new compounds of Formula I and pharmaceutically acceptable salts, hydrates, stereoisomers, optically active and geometrical isomers and tautomeric forms thereof.

(I)

wherein
R is hydrogen or lower alkyl;
$R^1$ is hydrogen, lower alkyl, styryl, carboxyl or a carboxylic acid derivative; or
R and $R^1$ together form a group of the formula —(CH=CH)$_2$— and in this case the broken line represents a further C—C bond, while in all other cases there is a single bond between positions 6 and 7;
$R^2$ is hydrogen, lower alkyl or hydroxy;
$R^3$ is hydrogen, lower alkyl, aryl, lower alkanoyl, carboxyl or a carboxylic acid derivative or a group of the formula —(CH$_2$)$_m$—COOH or a derivative thereof formed on the carboxylic group; m=1–3;
$R^4$ is hydrogen, lower alkyl which can be optionally substituted by hydroxy or carboxy; trifluoromethyl, substituted or unsubstituted aryl, phenyl-lower alkyl or a substituted or unsubstituted heterocyclic group;
$R^5$ is hydrogen, lower alkanoyl, substituted or unsubstituted benzoyl or heteroraryl; or $R^4$ and $R^5$ together with the adjacent nitrogen atom form a piperidino, pyrrolidino or morpholino ring; or $R^4$ and $R^5$ together with the adjacent nitrogen atom form a group of the formula $$-N=C\begin{matrix}R^6\\R^7\end{matrix}$$

wherein $R^6$ is hydrogen and $R^7$ is substituted or unsubstituted phenyl;
Z is oxygen and
n=1.

The term "lower alkyl" used throughout the specification—in itself or in combinations such as "lower alkoxy"—means straight or branched chain saturated aliphatic hydrocarbon groups having 1–6, preferably 1–4 carbon atoms (e.g. methyl, ethyl, n-propyl, isopropyl, n-butyl, secondary butyl, tertiary butyl, n-pentyl, neopentyl or n-hexyl).

The term "derivative of the carboxylic group" or "carboxylic acid derivative" covers usual carboxylic acid derivatives e.g. lower alkoxy-carbonyl, aryloxycarbonyl, aralkoxycarbonyl or other ester groups, a carbamoyl group optionally mono- or disubstituted by lower alkyl, aryl or aralkyl groups; cyano, carboxylic acid hydrazido or hydroxamic acid (—CO—NHOH).

The term "aryl"—used in itself or in combinations such as "aryloxy group"—means optionally substituted aromatic groups having 6 or 10 carbon atoms (e.g. phenyl or naphthyl or substituted derivatives thereof).

The term "aralkyl"—used in itself or in combinations such as "aralkoxy"—means an alkyl group having 1–3 carbon atoms substituted by phenyl or naphthyl groups (e.g. benzyl, α-phenyl-ethyl, α,β-diphenyl-ethyl or β,β-diphenyl-ethyl).

The term "optionally substituted alkyl group" or "substituted alkyl" means an alkyl groups substituted by hydroxy, halogen, carboxyl or a carboxylic acid derivative, amino, substituted amino, alkoxy or alkanoyloxy (e.g. trifluoromethyl, hydroxymethyl, aminoethyl, carboxy-methyl or β-carboxyethyl).

The term "aroyl" means acid radicals of aromatic carboxylic acids (e.g. optionally substituted benzoic acid).

The term "heteroaryl" as referred to acid radicals applies to heterocyclic carboxylic acids (e.g. pyridine-2-, -3- or 4-carboxylic acid, furane-carboxylic acid etc.).

The term "heterocyclic group" or "heterocycles" means mono- or bicyclic, optionally substituted unsaturated partly or completely saturated rings containing 1–4 nitrogen, oxygen and/or sulfur hetero atoms (e.g. thienyl, furyl, pyrrolyl, pyridyl, pyrimidinyl, pyrazinyl, pyridazinyl, quinolyl, isoquinolyl, benzofuranyl, benzoxazolyl, oxazolyl, oxadiazolyl, imidazolyl, benzimidazolyl, indolyl, benzothiazolyl, benzisothiazolyl, tetrazolyl, thiadiazolyl, triazinyl, piperidinyl, morpholinyl, pyrrolidinyl, piperazinyl or N-methyl-piperazinyl).

The term "heteroaryl" used throughout the specification refers to mono- or bicyclic optionally substituted aromatic rings containing 1–4 nitrogen, oxygen and/or sulfur heteroatoms (e.g. thienyl, furyl, pyrrolyl, pyridyl, pyrimidinyl, pyrazinyl, pyridazinyl, quinolyl, isoquinolyl, benzofuranyl, benzoxazolyl, oxazolyl, oxadiazolyl, imidazolyl, benzimidazolyl, indolyl, benzothiazolyl, benzisothiazolyl, tetrazolyl, thiadiazolyl, triazinyl).

The term "lower alkanoyl" means acid radicals of alkanoic acids having 1–6 carbon atoms (e.g. formyl, acetyl, propionyl, butyryl).

The aryl groups, the aryl ring of the aralkyl groups and the heterocyclic groups may optionally bear one or more suitable substituents e.g. one or more of the following groups and atoms: halogen (e.g. chlorine, bromine, iodine or fluorine), lower alkyl (e.g. methyl, ethyl), lower alkoxy (e.g. methoxy, ethoxy), lower alkylenedioxy (e.g. methylenedioxy, ethylenedioxy or propylenedioxy), amino, alkanoylamino, substituted amino, carboxyl or a carboxylic acid derivative, sulfonic acid or a salt or ester thereof, hydroxy, alkanoyloxy, aroyloxy, heteroaroyloxy, nitro, mercapto, lower alkylthio group.

Preferred representatives of the compounds prepared by the process of the present invention are those derivatives in which R is hydrogen $R^1$ is hydrogen, lower alkyl (preferably methyl), styryl, or lower alkoxycarbonyl (preferably methoxycarbonyl or ethoxycarbonyl);

$R^2$ is hydrogen, lower alkyl (e.g. methyl) or hydroxy;

$R^3$ is carboxyl, lower alkoxycarbonyl (preferably methoxycarbonyl or ethoxycarbonyl), carbamoyl, cyano, formyl, lower alkyl (e.g. methyl) or phenyl; or $R^4$ is hydrogen, lower alkyl (preferably methyl), hydroxyethyl, carboxyalkyl, optionally substituted phenyl or naphthyl, trifluoromethyl, benzyl, 2-, 3- or 4-pyridyl, benzothiazol-2-yl, methoxycarbonyl or ethoxycarbonyl;

$R^5$ is hydrogen, lower alkanoyl (preferably acetyl), benzoyl or nicotinoyl; or the grouping of the formula $-NR^4R^5$ is piperidinyl, pyrrolidinyl, morpholinyl or a group of the formula $-N=CR^6R^7$, wherein $R^6$ is hydrogen and $R^7$ is substituted or unsubstituted phenyl;

$R^4$ is particularly preferably phenyl which can bear in the ortho-, meta- and/or para-positions one, two or three of the following substituents: hydroxy group, halogen atom, lower alkyl, sulfonic acid, carboxylic group or a derivative thereof, alkoxy, alkylenedioxy, amino, substituted amino, nitro or trifluoromethyl.

Compounds corresponding to the following substituent definition constitute a class of compounds of formula I having particularly preferable properties:

R is hydrogen;
$R^1$ is methyl attached to position 6;

$R^2$ is hydrogen;
$R^3$ is a carboxylic group;
$R^4$ is optionally substituted phenyl;
$R^5$ is hydrogen;
Z is oxygen;
n=1; and
pharmaceutically acceptable salts thereof.

The compounds of formula I form salts with pharmaceutically acceptable organic or inorganic acids (e.g. hydrochlorides hydrobromides, hydroiodides, sulfates, nitrates, phosphates or maleates, succinates, acetates, tartarates, lactates, fumarates, citrates).

Compounds of formula I containing a carboxylic group or a sulfonic acid group can form salts with pharmaceutically acceptable bases (e.g. alkali metal salts such as sodium or potassium salts; alkaline earth metal salts such as calcium or magnesium salts; ammonium salts, salts formed with organic amines e.g. triethylamine salts, ethanolamine salts etc.

The present invention encompasses the preparation of optical and geometrical isomers and tautomeric forms of the compound of formula I. The structure of the geometrical isomers is shown by the formulae (IA) and (IB)

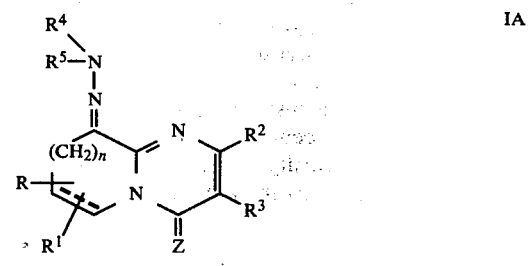

IA

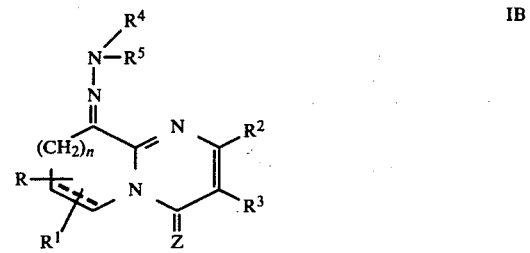

IB

The structure of the tautomers is illustrated on Reaction-scheme A:

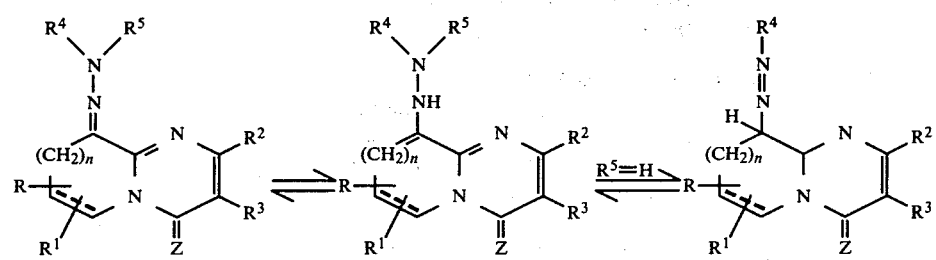

Compounds of formula I in which $R^2$ stands for a hydroxy group may show keto-enol tautomery as illustrated on Reaction scheme B:

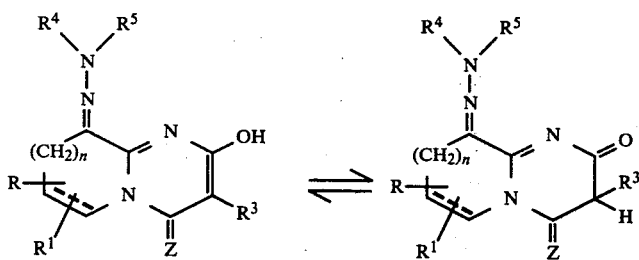

(In these formulae the substituents have the same meaning as stated above)

According to the process of the present invention compounds of formula I, pharmaceutically acceptable salts, hydrates, optically active geometrical and stereo isomers and tautomers thereof may be prepared by (a) for the preparation of compounds of formula I, wherein $R^4$ is an optionally substituted aryl or heteroaryl group and $R^5$ is hydrogen, reacting a compound of formula II

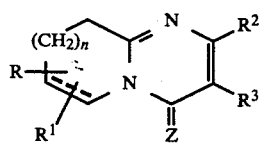

(II)

(wherein R, $R^1$, $R^2$, $R^3$, Z, n and the broken line have the same meaning as stated above) with a diazonium salt of formula III

   (III)

or a reactive derivative thereof (wherein Ar stands for an optionally mono- or polysubstituted aryl or heteroaryl group); or (b) reacting the compound of formula II (wherein R, $R^1$, $R^2 R^3$, Z, n and the broken line have the same meaning as stated above) with a compound of formula IV

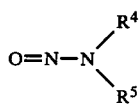   (IV)

(wherein $R^4$ and $R^5$ have the same meaning as stated above), or for the preparation of compounds of formula I, wherein $R^5$ is hydrogen, with a reactive derivative thereof; or (c) reacting a compound of formula V

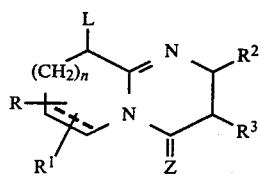   (V)

(wherein R, $R^1$, $R^2$, $R^3$, Z, n and the broken line have the same meaning as stated above and L is a leaving group) with a compound of formula VI

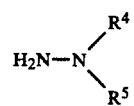   (VI)

(wherein $R^4$ and $R^5$ have the same meaning as stated above) and oxidizing the intermediate product thus formed after or without isolation; or (d) reacting a compound of formula VII

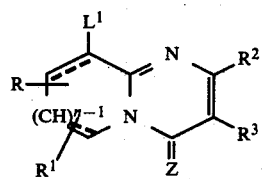   (VII)

(wherein R, $R^1$, $R^2$, $R^3$, Z, n and the broken line have the same meaning as stated above and $L^1$ is a leaving group) or a tautomer thereof with a compound of formula VI (wherein $R^4$ and $R^5$ have the same meaning as stated above); or (e) reacting a compound of formula VIII

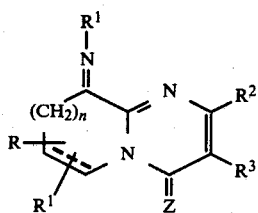   (VIII)

(wherein R, $R^1$, $R^2$, $R^3$, Z, L, n and the broken line have the same meaning as stated above) with an amine of the formula IX

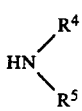   (IX)

or a salt thereof (wherein $R^4$ and $R^5$ have the same meaning as stated above); or (f) for the preparation of compounds of formula I, wherein $R^5$ is hydrogen, reacting a compound of formula X

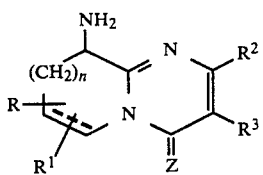

(wherein R, $R^1$, $R^2$, $R^3$, Z, n and the broken line have the same meaning as stated above) with a compound of formula XI $$O=N-R^4 \qquad (XI)$$

(wherein $R^4$ has the same meaning as stated above); or (g) for the preparation of compounds of formula I wherein $R^4$ is an optionally substituted aryl or heteroaryl group and $R^5$ is hydrogen, reacting a compound of formula XII

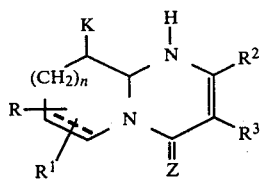

(wherein R, $R^1$, $R^2$, $R^3$, Z, n and the broken line have the same meanings as stated above and K is a leaving group) with a diazonium salt of formula III (wherein Ar has the same meaning as stated above) or a reactive derivative thereof and subjecting the intermediate product thus formed after or without isolation to removal of the K leaving group;

If desired subjecting a compound of formula I thus obtained to one or more of the following subsequent transformations: converting an $R^1$, $R^2$, $R^3$, $R^4$, and/or $R^5$ group into another $R^1$, $R^2$, $R^3$, $R^4$, and/or $R^5$ group by methods known per se; converting a compound of formula I which contains an acidic group into a salt formed with a pharmaceutically acceptable base; converting a compound of formula I of basic character into an addition salt formed with a pharmaceutically acceptable acid; setting free a compound of formula I from its salt formed with an acid or a base; and separating a racemic compound of formula I into its optically active antipodes.

According to variant (a) of our process compounds of formula I, wherein $R^4$ is an optionally substituted aryl or heteroaryl group and $R^5$ is hydrogen, are prepared by reacting a compound of formula II with a diazonium salt of formula III or a reactive derivative thereof. As reactive diazonium salt derivative a compound of formula XIII

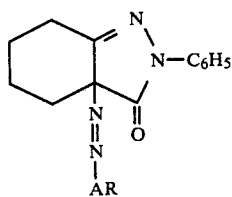

(wherein Ar has the same meaning as stated above) or another derivative described in Org. Reactions, Vol. 10, 147 (1959) John Wiley and Sons Inc., London) may be used. The reaction may be carried out at a temperature below 50° C., preferably 0°–20° C. The admixture of the components may be carried out in two ways: either the compound of formula II is added to the acidic diazonium salt solution or vice versa. The components may be advantageously used in equimolar ratio but any component may be applied in a small excess as well. The reaction may be optionally carried out in the presence of an acid-binding agent (e.g. sodium acetate). The reaction may be preferably accomplished in an aqueous medium generally used in reactions carried out with diazonium salts.

According to variant (b) of our process compounds of formula I, wherein $R^5$ is hydrogen are prepared by reacting a compound of formula II with a compound of formula IV or a reactive derivative thereof. Any reactive derivative of a compound of formula XIV

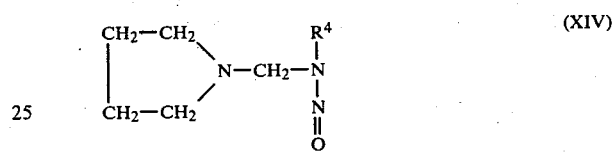

(wherein $R^4$ has the same meaning as stated above) or any derivative described in Chem. Pharm. Bull., 25, 731–9 (1977) may be used. The reaction may be carried out in an inert organic solvent. As reaction medium preferably aromatic hydrocarbons (e.g. benzene, toluene, xylene), pyridine, alkanols (e.g. methanol, ethanol) may be used. The reaction may be accomplished at elevated temperature preferably at the boiling point of the reaction mixture. The water formed in the reaction may be removed by azeotropic distillation (benzene, toluene) or with the aid of a dehydrating agent (e.g. dicyclohexylcarbodiimide).

In the starting materials of formula V used in variant (c) of our process L represents a conventional leaving group, such as halogen, (e.g. chlorine or bromine), alkylsulfonyloxy (e.g. methanesulfonyloxy), optionally substituted arylsulphonyloxy (e.g. p-toluene-sulphonyloxy or p-bromo-phenylsuflonyloxy group) or an alkanoyloxy group (e.g. acetoxy group). The reaction between the compounds of formulae V and VI is carried out preferably in the presence of an acid-binding agent. For this purpose preferably alkali metal carbonates (e.g. sodium or potassium), alkali metal bi-carbonates (e.g. sodium or potassium bi-carbonate), alkali metal salts of weak organic acids (e.g. sodium acetate) or the excess of the amine starting material of formula VI are used. The reaction can be accomplished in an inert solvent. As a reaction medium preferably aromatic hydrocarbons (e.g. benzene, toluene, xylene), esters (e.g. ethyl acetate), alcohols (e.g. methanol, ethanol) or dimethylformamide can be used. The reaction can be carried out at 0°–200° C., preferably at room temperature or with heating or at the boiling point of the reaction mixture, respectively.

In the above reaction presumably intermediate compounds of formula XV are formed

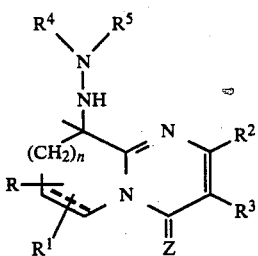 (XV)

(wherein R, $R^1$, $R^2$, $R^3$, $R^4$, $R^5$, Z, n and the broken line have the same meanings stated above) which are converted into the desired end products of formula I—after or without isolation—by means of oxidation. The intermediates of formula XV are preferably not isolated but the reaction mixture containing the said intermediates is subjected to the effect of the oxygen content of air at room temperature or under heating whereby oxidation takes place.

According to variant (d) of our process a compound of formula VII or a tautomer thereof is reacted with a compound of formula VI. The symbol $L^1$ in formula VII represents a conventional leaving group, such as halogen (e.g. chlorine or bromine atom), alkylsulfonyloxy (e.g. methanesulfonyloxy), optionally substituted arylsulfonyloxy (e.g. p-toluenesulfonyloxy or p-bromo-phenyl-sulfonyloxy group), alkanoyloxy (e.g. acetoxy) or hydroxy group. The reaction is preferably carried out in the presence of an acid binding agent. For this purpose advantageously alkali metal carbonates (e.g. sodium or potassium carbonate), alkali metal bicarbonates (e.g. sodium or potassium bi-carbonate), alkali metal salts of weak organic acids (e.g. sodium acetate) or an excess of the amine starting material of formula VI may be used. The reaction can be carried out in an inert solvent. As the reaction medium, preferably aromatic hydrocarbons (e.g. benzene, toluene, xylene), esters (e.g. ethyl acetate), alcohols (e.g. methanol, ethanol), or dimethylformamide can be used. The reaction can be carried out at 0°–200° C., preferably at room temperature or under heating or at the boiling point of the reaction mixture, respectively.

When starting materials of formula VII are used, wherein $L^1$ is a hydroxy group, the reaction is carried out preferably in the presence of a dehydrating agent (e.g. dicyclohexylcarbodiimide).

According to variant (e) of our process compounds of formulae VIII and IX are reacted under the conditions disclosed under reaction variant (d). The amine of formula IX can be used in the form of its salt (e.g. carbonate) too.

According to variant (f) of our process the compounds of the formulae X and XI are reacted preferably in an inert solvent. As the reaction medium aromatic hydrocarbons (e.g. benzene, toluene, xylene), alkanols (e.g. methanol, ethanol), esters (e.g. ethyl acetate) and ethers (e.g. dioxane) can be used. The reaction is preferably carried out in the presence of a dehydrating agent (e.g. dicyclohexylcarbodiimide). The reaction temperature is 0°–200° C., depending on the solvent used. One preferably works with heating.

According to variant (g) of our process a compound of formula XII is reacted with a dizonium salt of formula III or a reactive derivative thereof, whereafter the K leaving group is removed from the intermediate product formed after or without isolation. In the starting materials of formula XII, K stands for any easily removable leaving group, such as formyl, lower alkanoyl (e.g. acetyl), optionally substituted aroyl (e.g. benzoyl), or heteroaroyl or carboxylic group or a derivative thereof (e.g. carboxylic acid ester, carbamoyl, substituted carbamoyl, acid azide or cyano). The reactive derivatives of the diazonium salts of formula III can be those set forth in reaction variant (a). The reaction can be carried out in water or a mixture of water and a water-miscible organic solvent (e.g. alkanols, pyridine). The reaction can be optionally accomplished in the presence of an acid binding agent. For this purpose e.g. sodium acetate or alkali metal hydroxides can be used. The reaction can be carried out at a temperature below 5° C., preferably at 0°–20° C.

The intermediate compounds formed in the above reaction correspond presumably to formula XVI

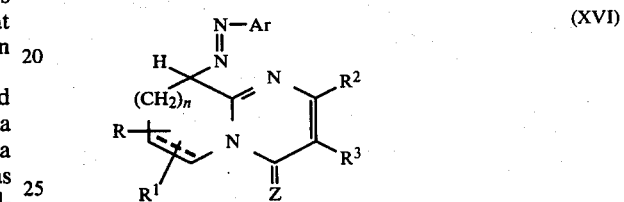 (XVI)

(wherein R, $R^1$, $R^2$, $R^3$, K, Z, n and the broken line have the meaning as stated above). These compounds may be converted into the end-products of formula I by acidic or alkaline treatment as described in Org. Reactions Vol. 10, 143–178 (1959) John Wiley and Sons, Inc., London, in connection with the JappKlingmann reaction. According to reaction variant (g) compounds of formula I are obtained, wherein $R^4$ is an optionally substituted aryl or heteroaryl group and $R^5$ is hydrogen.

The compounds of formula I obtained by the above reaction variants may be isolated from the reaction mixture by methods known per se. The compounds of formula I often precipitate from the reaction mixture in the form of their salt or hydrate and may be separated by means of filtration or centrifuging. If the reaction is carried out in aqueous medium the end product is extracted from the reaction mixture with suitable organic solvent (e.g. benzene, chloroform, ether) and isolated by evaporating the organic extract. If the reaction is carried out in an organic medium the compound of formula I can be isolated by removing the organic solvent. The compounds of formula I may be purified by recrystallization or by means of chromatography, if necessary.

The compounds of formula I thus obtained can be converted into another compound of the formula I by one or more subsequent transformations carried out by methods known per se. Said transformation can be carried out at the $R^1$, $R^2$, $R^3$, $R^4$, and/or $R^5$ group. Subsequent transformation can be carried out by means of reactions and under conditions conveniently used in reactions of such types.

A carboxylic group standing for $R^1$, $R^2$, $R^3$ or being present in group $R^4$ or $R^5$ can be converted into an alkaoxycarbonyl, aryloxycarbonyl or aralkyloxycarbonyl group by esterification reactions known per se. Esterification can be carried out e.g. by reacting the carboxylic acid with the corresponding alcohol or phenol in the presence of an acidic catalyst (e.g. concentrated sulfuric acid) or with a diazoalkane (e.g. diazomethane, diazoethane).

Compounds containing a carboxylic group may be subjected to decarboxylation by heating whereby the corresponding compounds containing a hydrogen atom at the place of the carboxylic group are obtained; decarboxylation is preferably carried out in the presence of an acid (e.g. phosphoric acid).

A derivative containing a carboxylic group may be converted into an optionally substited acid amide by reacting with the corresponding amine. Substituted acid amides can be prepared in a manner known per se through an active ester (e.g. ethylchloroformate).

An ester group at $R^1$, $R^2$ or $R^3$ or being present in the group $R^4$ or $R^5$ can be subjected to trans-esterification by heating with an excess of the corresponding alcohol. An ester of formula I can be converted into the corresponding free carboxylic acid by acidic or alkaline treatment. Alkaline hydrolysis can be carried out by heating with an alkali metal hydroxide in an aqueous or alkanolic medium and setting free the carboxylic acid from the alkali metal salt formed by acidification. Hydrolysis carried out with a mineral acid directly leads to the formation of the free carboxylic acid.

An ester of formula I can be converted into the corresponding acid amide of formula I by reaction with ammonia in aqueous-alcoholic medium or into the dorresponding hydrazide of formula I by reaction with an optionally substituted hydrazine (e.g. hydrazine, methyl- or phenyl-hydrazine).

A cyano group at $R^1$, $R^2$ or $R^3$ or in group $R^4$ or $R^5$ can be converted into a carboxylic group by heating with concentrated alkali metal hydroxide, or can be transformed into an acid amide (carbamoyl) group by acidic hydrolysis cold or by alkaline hydrolysis at a temperature of about 50° C. (Alkaline hydrolysis is preferably carried out in the presence of hydrogen peroxide.)

A carbamoyl group at $R^1$, $R^2$ or $R^3$ or in group $R^4$ or $R^5$ can be converted into a carboxylic group by heating in alkaline or acidic medium. The hydrolysis of acid amides which do not readily hydrolyze can be carried out in the presence of nitric acid.

The carboxylic acid hydrazides of formula I can be hydrolized into the corresponding carboxylic acids of formula I by warming in the presence of an acid or an alkali.

Compounds of formula I, wherein $R^5$ is hydrogen, can be acylated into the corresponding compounds of formula I, wherein $R^5$ is formyl, alkanoyl, aroyl or heteroaroyl group. Acylation can be carried out by methods known per se by using the corresponding carboxylic acid or a reactive derivative thereof. As the acylating agent, preferably acid halides (e.g. acid chlorides), acid anhydrides or active esters (e.g. pentachlorophenyl esters) can be used. Acylation is preferably accomplished in the presence of an acid binding agent (e.g. triethylamine). If acylation is carried out with a free carboxylic acid, the reaction can be advantageously accomplished in the presence of a dehydrating agent (e.g. dicyclohexylcarbodiimide). Acylation can be carried out by methods and acylating agents well known in peptide chemistry.

Compounds of formula I, wherein $R^4$ and $R^5$ are hydrogen can be condensed with an aldehyde to yield the corresponding compound of formula I, wherein the group $-NR^4R^5$ is a group of the formula $-N=CR^6R^7$. Condensation can be carried out in an inert solvent (e.g. benzene, toluene) at room temperature or under heating. The water formed in the reaction can be removed in the form of an azeotropic mixture or with the aid of a dehydrating agent. As the aldehyde or ketone, e.g. acetone, acetaldehyde or benzaldehyde can be used.

An aryl group at $R^4$ and/or $R^5$ can be subjected to one or more known transformations. Thus a compound of formula I, wherein $R^4$ and/or $R^5$ is an unsubstituted phenyl group can be nitrated with a mixture of nitric acid and sulfuric acid, the nitro derivative thus obtained can be optionally reduced (e.g. by catalytic hydrogenation) and the amino derivative thus obtained can be optionally alkylated or acylated.

The subsequent transformation reactions form also part of the present invention.

A compound of formula I can be set free from its salt formed with an acid or a base by methods known per se.

A compound of formula I of basic character can be converted into an addition salt formed with an inorganic or organic acid. Salt formation can be carried out in a known manner by reacting the compound of formula I with the corresponding acid—used in equimolar amount or in excess—in an inert organic solvent.

Compounds of formula I, which contain an acidic group (a carboxylic or sulfonic group) can be converted into their salts by reaction with the corresponding base (e.g. alkali metal hydroxides, alkaline earth metal hydroxides, organic amines) in a manner known per se.

Compounds of formula I, in which R and/or $R^1$ are other than hydrogen contain a chiral(asymmetric) center and can be present in the form of an optically active antipode or a racemate. The optically active antipodes of the above compound of formula I can be prepared either by using in the reaction variants (a) and (g) an optically active starting material of formulae II, V, VII, VIII, X or XII or by subjecting a racemic compound of formula I to resolution. The resolution can be carried out by methods known per se. Compounds of formula I containing a carboxylic group can be separated into the optically active antipodes e.g. by reacting the racemate with a suitable optically active base (such as optically active threo-1-(p-nitro-phenyl)-2-amino-propane-1,3-diol), separating the members of the diastereomeric salt pair thus formed on the basis of their different physical properties (e.g. by crystallization) and thereafter setting free the optically active antipode of formula I from the salt by reaction with a strong base.

The nitrogen bridge-head starting mateials used are partly known. The starting materials of formulae II, VII and X are known from prior art (*Arzneimittelforschung*, 22, 815, 1972) or can be prepared by analogous methods. The starting materials of formula V can be prepared from the compounds of formula II by halogenation. The starting materials of formula VII can be prepared by reacting a compound of formula V with a compound of formula IX and subjecting the condensation product thus obtained to oxidation. The starting materials of formula XII can be prepared by reacting a compound of formula II with a Vielsmeyer-Haack reactant or with phosgene ammonium chloride and subjecting the compound thus obtained to further transformation.

The starting materials of formulae III, IV, VI, IX and XI are well known from the literature and generally are commercially available or can be readily prepared from commercially available compounds by methods known per se.

The compounds of formula I exhibit anti-inflammatory, analgesic, thrombus-aggregation inhibiting, anti-atherogenic, heart function and circulation influencing, tranquilizing, central nervous system influencing, PG-antagonistic, antiulcus, antibacterial and antifungal effect and can be used in human and veterinary therapy. The anti-allergic and antiasthmatic effects of the compounds of formula I are particularly remarkable.

Allergic reactions induced by antigen-antibody interaction can manifest themselves in different organs and tissues. Asthma is the most common form of allergy. Disodium-chromoglycate [1,3-bis-(2-carboxy-chromon-6-yl-oxy)-2-hydroxy-propane, Intal[R]] is generally used as anti-asthmatic agent but this compound is ineffective when administered orally and exhibits the desired effect only when administered by inhalation with the aid of a complicated therapeutic device (spinhaler). It has been found that the new compounds of formula I cure allergic symptoms with excellent results when administered either orally or intravenously or by inhalation.

The activity of the compounds of formula I was proved by standard tests used for the determination of anti-allergic effect. The PCA text (*Ovary; J. Immun.* 81, 355, 1958) and the Church test (*British J. Pharm.* 46, 56–66, 1972); *Immunology* 29, 527–534, 1975) were used. The tests were carried out on rats. The results are summarized in Table I.

TABLE 1

| Test Compound Example No. | PCA test ED$_{50}$ $\mu$M/kg i.v. | PCA test $\mu$M/kg p.o. | Church test ED$_{50}$ $\mu$M/kg i.v. |
|---|---|---|---|
| 14 | 0.60 | 1.2 | 0.31 |
| 37 | 0.29 | 1.0 | 0.14 |
| Disodium-chromoglycate | 1.00 | ineffective | 0.84 |

| Test Compound Example No. | PCA test Ed$_{50}$ i.v. $\mu$M/kg | Released Hist. in vitro EC$_{50}$ $\mu$M/L |
|---|---|---|
| 18 | 0.53 | 100 |
| 23 | 0.53 | 120 |
| 41 | 1.0 | |
| 50 | 0.42 | |
| 45 | 0.61 | |
| 43 | 0.57 | |

| Test Compound Example No. | PCA test Percentage of activity for a single dose of 320 $\mu$M/kg | Released Hist. in vitro EC$_{50}$ $\mu$M/L |
|---|---|---|
| 26 | 89 | 90 |
| 35 | 100 | 17.6 |
| 16 | 100 | 2 |
| 41 | 100 | 100 |
| 48 | 100 | 100 |
| 50 | 100 | 73 |
| 45 | 100 | 312 |
| 43 | 100 | 100 |

| Test Compound Example No. | PCA test I.v. $\mu$M/kg | Histamine liberation in vitro EC$_{50}$ $\mu$M/L |
|---|---|---|
| 45 | | 311.9 |
| 48 | 7.6 | 100 |
| 50 | | 72.9 |

Pharmacological data

The ED$_{50}$ data of further compounds of the formula I tested in the PCA test are summarized in the following Table:

| Compound | ED$_{50}$ $\mu$M/kg i.v. |
|---|---|
| 9-[(2-carboxy-phenyl)-hydrazono]-6-methyl-4-oxo-6,7,8,9-tetrahydro-4H—pyrido(1,2-a)pyrimidine-3-carboxylic acid | 0.48 |
| 9-[(4-ethoxy-phenyl)-hydrazono]-6-methyl-4-oxo-6,7,8,9-tetrahydro-4H—pyrido(1,2-a)pyrimidine-3-carboxylic acid | 1.0 |
| 9-[(4-chloro-phenyl)-hydrazono]-6-methyl-4-oxo-6,7,8,9-tetrahydro-4H—pyrido(1,2-a)pyrimidine-3-carboxylic acid | 0.53 |
| 9-(3-pyridyl-hydrazono)-6-methyl-4-oxo-6,7,8,9-tetrahydro-4H—pyrido(1,2-a)pyrimidine-3-carboxylic acid | 0.54 |

It appears from the above data that the representatives of the compounds prepared according to the present invention are also active when administered orally, contrary to the disodium chromoglycate, which proved to be effective only when administered intravenously. The compounds of formula I are more active than the known reference compound also when administered intravenously.

The toxicity of the compounds of formula I is low, the LD$_{50}$ value is generally above 500 mg./kg. p.o. on rats and mice.

The compounds of formula I can be used in the therapy in the form of pharmaceutical compositions containing these active ingredients in admixture with solid or liquid, organic or inorganic carriers. The compositions are prepared by methods known per se in the pharmaceutical industry.

The compositions may be suitable for oral or parenteral administration or may be used for inhalation and may be finished in the form of tablets, dragées, capsules, lozenges, powder mixtures aerosol spray, aqueous suspension or solution or injectable solution or syrups. The compositions may contain suitable solid diluents or carriers, sterile aqueous solvent or nontoxical organic solvent. To the oral compositions sweetening or flavoring agents used for such purposes may be added.

Tablets suitable for oral administration may contain carriers (e.g. lactose, sodium citrate, calcium carbonate), desintegrating agents (e.g. starch, alginic acid), sliding agents (e.g. talc, sodium lauryl sulfate, magnesium stearate). The carrier of the capsules may generally be lactose or polyethyleneglycol. The aqueous suspensions may contain emulsifying or suspending agents. The diluent of suspensions formed with organic solvents may be ethanol, glycerol or chloroform etc.

Compositions for parenteral administration or inhalation comprise the solution or suspension of the active ingredient in a suitable medium (e.g. coconut oil, sesame oil, polypropyleneglycol or water). The injectable compositions may be administered intramuscularly, intravenously or subcutaneously. The injectable solutions are preferably prepared in aqueous media and the pH is adjusted to a suitable value. The solutions may be prepared in an isotonic salt or glucose solution, if necessary.

The compositions may be applied into the organism for the treatment of asthma also by inhalation by means of conventional inhalating and nebulizing apparatus.

The active ingredient content of the pharmaceutical compositions may vary between wide ranges and may be from 0.005% to 90%.

The daily active ingredient dosage may also vary between wide ranges and depends on the condition, age and weight of the patient, the mode of finishing and the efficiency of the given active ingredient. In the case of oral administration the daily active ingredient dosage is generally 0.05–15 mg./kg., while when administered by inhalation or intravenously it amounts to 0.001–5 mg./kg; the said dosage may be administered at once or in several portions. The above ranges are but of informative character and the actual dose used may be lower or higher, depending on the prescriptions of the physician and the circumstances of the given case.

Further details of the present invention are to be found in the examples. It is, however, by no means intended to limit our invention to the examples.

EXAMPLE 1

To a mixture of 18.6 g. (0.2 mole) of aniline and 100 ml. of a 1:1 diluted aqueous hydrochloric acid a solution of 13.8 g. (0.2 mole) of sodium nitrite and 100 ml. of water is slowly added at 0°–5° C. under stirring dropwise. Thereafter to the reaction mixture a solution of 47.2 g. (0.2 mole) of ethyl-6-methyl-4-oxo-6,7,8,9-tetrahydro-4H-pyrido(1,2-a)pyrimidine-3-carboxylate in 100 ml. of water is slowly added dropwise under vigorous stirring. The reaction mixture is stirred at 0°–5° C. for 2–3 hours whereupon it is allowed to stand in a refrigerator overnight. The precipitated crystals are filtered off and washed with some water. The substance thus obtained is treated with 500 ml. of water and 500 ml. of chloroform, whereupon the pH of the aqueous phase is adjusted to 7 with a 5 weight/volume % aqueous sodium carbonate solution. The organic layer is separated and the aqueous phase is extracted twice with 500 ml. of chloroform each. The united organic phase is dried over anhydrous sodium sulfate and the solvent is removed in vacuo. The residual red oil is crystallized from a 2–3-fold amount of ethanol.

Yield: 48.7 g. (63.0%). Mp.: 86°–87° C.

The product crystallizes with 1 mole of ethanol and the ethanol content may be removed by drying in vacuo at 90°–100° C. over phosphorous pentoxide. The melting point of the dried ethyl-9-(phenyl-hydrazono)-6-methyl-4-oxo-6,7,8,9-tetrahydro-4H-pyrido(1,2-a)pyrimidine-3-carboxylate amounts to 138°–139° C.

Analysis for the formula $C_{18}H_{20}N_4O_3$: Calculated: C: 63.51%; H: 5.92%; N: 16.45%; Found: C: 63.53%; H: 6.03%; N: 16.60%.

EXAMPLE 2

6.3 g. (0.02 mole) of ethyl-9-bromo-6-methyl-4-oxo-6,7,8,9-tetrahydro-4H-pyrido(1,2-a)pyrimidine-3-carboxylate are dissolved in 30 ml. of anhydrous ethanol and 4.3 ml. (0.044 mole) of phenyl-hydrazine are added to the solution. The reaction mixture is heated to boiling for 4 hours whereupon the solvent is distilled off in vacuo. To the residue 30 ml. of water and 15 ml. of chloroform are added and the pH of the aqueous layer is adjusted to 2–3 with a 10 weight/volume % aqueous hydrochloric acid solution under stirring. The organic layer is separated and the aqueous phase is extracted twice with 15 ml. of chloroform each. The united organic layer is dried over anhydrous sodium sulfate and the solvent is removed in vacuo. The residual red oil crystallizes from a 2–3 fold amount of ethanol. Yield: 5.3 g. (68.6%). Mp.: 86°–87° C.

The product obtained crystallizes with 1 mole of ethanol which can be removed by drying in vacuo at 90°–100° C. over phosphorous pentoxide. The melting point of the dried ethyl-9-(phenyl-hydrazono)-6-methyl-4-oxo-6,7,8,9-tetrahydro-4H-pyrido(1,2-a)pyrimidine-3-carboxylate amounts to 138°–139° C. The product does not give a melting point depression when admixed with the compound prepared according to Example 1.

EXAMPLE 3

2.5 g, (0.01 mole) of ethyl-9-hydroxy-6-methyl-4-oxo-6,7-dihydro-4H-pyrido(1,2-a)pyrimidine-3-carboxylate are dissolved in 7.5 ml. of anhydrous ethanol. To the solution 1.2 ml. (0.012 mole) of phenyl-hydrazine are added. The reaction mixture is heated to boiling for half an hour, whereupon it is allowed to cool. Orange coloured crystals precipitate. Yield: 3.5 g. (90.6%). Mp.: 86°–87° C.

The product crystallizes with 1 mole of ethanol which can be removed by drying at 90°–100° C. over phosphorous pentoxide in vacuo. The melting point of the dried ethyl-9-(phenyl-hydrazono)-6-methyl-4-oxo-6,7,8,9-tetrahydro-4H-pyrido-(1,2-a)pyrimidine-3-carboxylate amounts to 138°–139° C. The product does not show a melting point depression when admixed with the compound prepared according to Example 1 or 2.

EXAMPLES 4–5

The process described in Example 1 is carried out except that aniline is replaced by p-bromo-aniline and m-toluidine, respectively. The following compounds are prepared:

(4) Ethyl-9-(p-bromo-phenyl-hydrazono)-6-methyl-4-oxo-6,7,8,9-tetrahydro-4H-pyrido(1,2-a)pyrimidine-3-carboxylate, mp.: 188°–189° C.

Analysis for the formula $C_{18}H_{19}N_4O_3Br$: Calculated: C: 51.69%; H: 4.34%; N: 13.39%; Br: 19.10%; Found: C: 51.84%; H: 4.54%; N: 13.26%; Br: 19.13%.

(5) Ethyl-9-(m-methyl-phenyl-hydrazono)-6-methyl-4-oxo-6,7,8,9-tetrahydro-4H-pyrido(1,2-a)pyrimidine-3-carboxylate, mp.: 159°–160° C.

Analysis for the formula $C_{19}H_{22}N_4O_3$: Calculated: C: 64.39%; H: 6.25%; N: 15.80%; Found: C: 64.30%; H: 6.22%; N: 15.85%.

EXAMPLE 6

To a mixture of 2.5 g. (0.02 mole) of p-chloroaniline and 10 ml. of a 1:1 diluted aqueous hydrochloric acid a solution of 1.4 g. (0.01 mole) of sodium nitrite and 10 ml. of water is slowly added dropwise at 0°–5° C. under stirring. To the reaction mixture 12.0 g. of solid sodium acetate are added in portions, whereupon a solution of 4.7 g. (0.02 mole) of ethyl-6-methyl-4-oxo-6,7,8,9-tetrahydro-4H-pyrido(1,2-a)pyrimidine-3-carboxylate and 10 ml. of water is slowly added dropwise under vigorous stirring. The reaction mixture is stirred at 0°–5° C. for 2–3 hours, whereupon it is allowed to stand in a refrigerator overnight. The precipitated crystals are filtered off and washed with a small amount of water. After recrystallization from ethanol 4.2 g. (56.0%) of ethyl-9-(p-chloro-phenyl-hydrazono)-6-methyl-4-oxo-6,7,8,9-tetrahydro-4H-pyrido(1,2-a)pyrimidine-3-carboxylate are obtained. Mp.: 177°–178° C.

Analysis for the formula $C_{18}H_{19}N_4O_3Cl$: Calculated: C: 57.67%; H: 4.30%; N: 14.90%; Cl: 9.45%; Found: C: 57.35%; H: 4.40%; N: 15.04%; Cl: 9.57%.

EXAMPLE 7

To a mixture of 2.9 g. (0.02 mole) of p-toluidinemonohydrochloride and 6 ml. of a 1:1 diluted aqueous hydrochloric acid solution at 0°–5° C. under stirring a solution of 1.4 g. (0.02 mole) of sodium nitrite and 10 ml. of water is slowly added dropwise.

Thereafter one proceeds exactly as described in Example 5. Yield: 4.0 g. (56.4%) of ethyl-6-methyl-9-(p-methyl-phenyl-hydrazono)-4-oxo-6,7,8,9-tetrahydro-4H-pyrido(1,2-a)pyrimidine-3-carboxylate. Mp.: 147°–149° C.

Analysis for the formula $C_{19}H_{22}N_4O_3$: Calculated: C: 64.39%; H: 6.25%; N: 15.80%; Found: C: 64.05%; H: 6.34%; N: 15.71%.

EXAMPLES 8–13

The process described in Example 6 is carried out except that p-chloro-aniline is replaced by 2,6-dichloro-aniline, o-toluidine, 3,4-methylenedioxy-aniline, o-nitro-aniline, p-nitro-aniline and sulfanilamide, respectively. The following compounds are prepared.

(8) Ethyl-9-(2,6-dichloro-phenyl-hydrazono)-6-methyl-4-oxo-6,7,8,9-tetrahydro-4H-pyrido(1,2-a)pyrimidine-3-carboxylate, mp.: 153°–154° C.

Analysis for the formula $C_{18}H_{18}N_4O_3Cl_2$: Calculated: C: 52.82%; H: 4.43%; N: 13.68%; Cl: 17.32%; Found: C: 52.52%; H: 4.47%; N: 13.75%; Cl: 17.26%.

(9) Ethyl-6-methyl-9-(o-methyl-phenyl-hydrazono)-4-oxo-6,7,8,9-tetrahydro-4H-pyrido(1,2-a)pyrimidine-3-carboxylate, mp.: 185° C.

Analysis for the formula $C_{19}H_{22}N_4O_3$: Calculated: C: 64.39%; H: 6.25%; N: 15.80%; Found: C: 64.45%; H: 6.01%; N: 15.75%.

(10) Ethyl-6-methyl-9-(3,4-methylenedioxy-phenyl-hydrazono)-4-oxo-6,7,8,9-tetrahydro-4H-pyrido(1,2-a)pyrimidine-3-carboxylate, mp.: 172°–173° C.

Analysis for the formula $C_{19}H_{20}N_4O_5$: Calculated: C: 58.02%; H: 5.38%; N: 14.23%; Found: C: 58.22%; H: 5.39%; N: 14.35%.

(11) Ethyl-6-methyl-9-(o-nitro-phenyl-hydrazono)-4-oxo-6,7,8,9-tetrahydro-4H-pyrido(1,2-a)pyrimidine-3-carboxylate, mp.: 190°–192° C.

Analysis for the formula $C_{18}H_{19}N_5O_5$: Calculated: C: 56.10%; H: 4.96%; N: 18.17%; Found: C: 56.12%; H: 5.04%; N: 18.12%.

(12) Ethyl-6-methyl-9-(p-nitro-phenyl-hydrazono)-4-oxo-6,7,8,9-tetrahydro-4H-pyrido(1,2-a)pyrimidine-3-carboxylate, mp.: 218°–219° C.

Analysis for the formula $C_{18}H_{19}N_5O_5$: Calculated: C: 56.10%; H: 4.96%; N: 18.17%; Found: C: 55.98%; H: 4.80%; N: 18.03%.

(13) Ethyl-9-[p-(aminosulphonyl)-phenyl-hydrazono]-6-methyl-4-oxo-6,7,8,9-tetrahydro-4H-pyrido(1,2-a)pyrimidine-3-carboxylate-monohydrate, mp.: 210°–213° C.

Analysis for the formula $C_{18}H_{21}N_5O_5S \cdot H_2O$: Calculated: C: 49.42%; H: 5.30%; N: 16.01%; S: 7.33%; Found: C: 49.01%; H: 5.11%; N: 15.74%; S: 7.52%.

EXAMPLE 14

To a mixture of 93.1 g. (1.0 mole) of aniline and 480 ml. of a 1:1 diluted aqueous hydrochloric acid solution at 0°–5° C. under stirring a solution of 68.9 g. (1.0 mole) of sodium nitrite and 500 ml. of water is slowly added dropwise. Thereafter to the reaction mixture 65.0 g. of solid sodium acetate are added in portions.

To 208.2 g. (1.0 mole) of 6-methyl-4-oxo-6,7,8,9-tetrahydro-4H-pyrido(1,2-a)pyrimidine-3-carboxylic acid 500 ml. of water are added and the pH is adjusted to 7 with a 10 weight/volume % aqueous sodium carbonate solution; hereby a solution is formed. The said solution is slowly added dropwise under vigourous stirring to the previously prepared diazonium salt.

The reaction mixture is stirred at 0°–5° C. for 2–3 hours whereupon it is allowed to stand in a refrigerator overnight. The precipitated crystals are filtered off and washed with a small amount of water.

The crude product is dissolved in an aqueous sodium hydroxide solution and clarified with activated coal. The solution is then acidified and the precipitated crystals are filtered off. Yield: 293.0 g. (93.8%) of 9-(phenyl-hydrazono)-6-methyl-4-oxo-6,7,8,9-tetrahydro-4H-pyrido(1,2-a)pyrimidine-3-carboxylic acid. Mp.: 255°–256° C. (After recrystallization from dimethylformamide the melting point rises to 267°–268° C.)

Analysis for the formula $C_{16}H_{16}N_4O_3$: Calculated: C: 61.53%; H: 5.16%; N: 17.94%; Found: C: 61.62%; H: 5.26%; N: 18.10%.

EXAMPLE 15

To a solution of 0.6 g. (0.015 mole) of sodium hydroxide and 25 ml. of water 3.4 g. (0.01 mole) of ethyl-9-(phenyl-hydrazono)-6-methyl-4-oxo-6,7,8,9-tetrahydro-4H-pyrido(1,2-a)pyrimidine-3-carboxylate are added. The suspension formed is stirred at 50°–60° C. for 4–5 hours whereby a solution is obtained. The pH is adjusted to 2 by adding a 1:1 diluted aqueous hydrochloric acid solution. The precipitated crystals are filtered off and washed with a small amount of water. Yield: 2.7 g. (86.4%) of 9-(phenyl-hydrazono)-6-methyl-4-oxo-6,7,8,9-tetrahydro-4H-pyrido(1,2-a)pyrimidine-3-carboxylic acid. Mp.: 267°–268° C. The product does not give a melting point depression when admixed with the compound prepared according to Example 14.

EXAMPLE 16–23

The process according to Example 14 is carried out except that aniline is replaced by p-bromo-aniline, anthranilic acid, p-chloro-aniline, o-toluidine, 2,6-dimethyl-aniline, 2,4,5-trimethyl-aniline, 2,4,6-trimethyl-aniline and 3-amino-pyridine, respectively. The following compounds are prepared.

(16) 9-(p-bromo-phenyl-hydrazono)-6-methyl-4-oxo-6,7,8,9-tetrahydro-4H-pyrido(1,2-a)pyrimidine-3-carboxylic acid, mp.: 250°–252° C.

Analysis for the Formula $C_{17}H_{16}N_4O_5$: Calculated: C 49.12%; H: 3.86%; N: 14.32%; Br: 20.43%; Found: C: 48.90%; H: 3.86%; N: 14.36%; Br: 20.66%.

(17) 9-(o-carboxy-phenyl-hydrazono)-6-methyl-4-oxo-6,7,8,9-tetrahydro-4H-pyrido(1,2-a)pyrimidine-3-carboxylic acid, mp.: 266°–268° C.

Analysis for the formula $C_{17}H_{16}N_4O_5$: Calculated: C: 57.30%; H: 4.53%; N: 15.72%; Found: C: 57.87%; H: 4.40%; N: 15.62%.

(18) 9-(p-chloro-phenyl-hydrazono)-6-methyl-4-oxo-6,7,8,9-tetrahydro-4H-pyrido(1,2-a)pyrimidine-3-carboxylic acid, mp.: 262°–264° C.

Analysis for the formula $C_{16}H_{15}N_4O_3Cl$: Calculated: C: 55.42%; H: 4.36%; N: 16.16%; Cl: 10.22%; Found: C: 55.40%; H: 4.21%; N: 16.02%; Cl: 10.21%.

(19) 6-methyl-9-(o-methyl-phenyl-hydrazono)-4-oxo-6,7,8,9-tetrahydro-4H-pyrido(1,2-a)pyrimidine-3-carboxylic acid, mp.: 221°–223° C.

Analysis for the formula $C_{17}H_{18}N_4O_3$: Calculated: C: 62.57%; H: 5.56%; N: 17.17%; Found: C: 62.83%; H: 5.55%; N: 16.83%;

(20) 6-methyl-9-(2,6-dimethyl-phenyl-hydrazono)-4-oxo-6,7,8,9-tetrahydro-4H-pyrido(1,2-a)pyrimidine-3-carboxylic acid, mp.: 192°–193° C.

Analysis for the formula $C_{18}H_{20}N_4O_3$: Calculated: C: 63.14%; H: 5.88%; N: 16.36%; Found: C: 63.14%; H: 5.93%; N: 16.15%.

(21) 6-methyl-9-(2,4,5-trimethyl-phenyl-hydrazono)-4-oxo-6,7,8,9-tetrahydro-4H-pyrido(1,2-a)pyrimidine-3-carboxylic acid, mp.: 224°–226° C.

Analysis for the formula $C_{19}H_{22}N_4O_3$: Calculated: C: 62.78%; H: 6.28%; N: 15.81%; Found: C: 62.43%; H: 6.07%; N: 15.32%.

(22) 6-methyl-9-(2,4,6-trimethyl-phenyl-hydrazono)-4-oxo-6,7,8,9-tetrahydro-4H-pyrido(1,2-a)pyrimidine-3-carboxylic acid; mp.: 195°–197° C.

Analysis for the formula $C_{19}H_{22}N_4O_3$: Calculated: C: 62.78%; H: 6.26%; N: 15.81%; Found: C: 63.29%; H: 6.17%; N: 15.68%.

(23) 6-methyl-9-(3-pyridyl-hydrazono)4-oxo-6,7,8,9-tetrahydro-4H-pyrido(1,2-a)pyrimidine-3-carboxylic acid, mp.: 236°–237° C.

Analysis for the formula $C_{15}H_{15}N_5O_3$: Calculated: C: 57.50%; H: 4,83%; N: 22.35%; Found: C: 57.81%; H: 4.85%; N: 22.27%.

EXAMPLE 24

1.8 g. (0.01 mole) of 2,4-dinitro-aniline are dissolved in a mixture of 15 ml. of glacial acetic acid and 1.1 ml. of concentrated sulfuric acid. The solution is cooled to 10°–15° C. whereupon 0.7 g. (0.01 mole) of sodium nitrite are added under stirring in portions. The diazonium salt is precipitated by addition of ether, separated by decanting and dissolved in 10–15 ml. of ice-cold water.

Thereafter one proceeds as described in Example 14 except that no sodium acetate is added to the reaction mixture.

On recrystallizing the crude product from acetonitrile 0.8 g. (20.0%) of 6-methyl-9-(2,4-dinitro-phenyl-hydrazono)-4-oxo-6,7,8,9-tetrahydro-4H-pyrido(1,2-a)pyrimidine-3-carboxylic acid are obtained. Mp.: 257°–258° C.

Analysis for the formula $C_{16}H_{13}N_6O_7$: Calculated: N: 47.88%; H: 3.26%; N: 20.94%; Found: N: 47.44%; H: 3.39%; N: 20.66%.

EXAMPLE 25

A solution of 1.9 g. (0.01 mole) of sulfanilic acid, 0.8 g. (0.01 mole) of sodium bi-carbonate and 0.7 g. (0.01 mole) of sodium nitrite in 10 ml. of water is added dropwise at 0°–5° C. under stirring to 5 ml. of a 1:1 diluted aqueous hydrochloric acid solution. Thereafter one proceeds in the same manner as described in Example 14. The crude product is recrystallized from a 75% aqueous methanol. Yield: 0.3 g. (7.6%) of 6-methyl-4-oxo-9-(p-sulfo-phenyl)-hydrazono-6,7,8,9-tetrahydro-4H-pyrido(1,2-a)pyrimidine-3-carboxylic acid. Mp.: above 290° C.

Analysis for the formula $C_{16}H_{16}N_4O_6S$: Calculated: C: 48.98%; H: 4.11%; N: 14.28%; S: 8.17%; Found: C: 49.11%; H: 4.10%; N: 14.21%; S: 8.25%.

EXAMPLE 26

To 780 ml. of methanol, 80.0 g. (0.28 mole) of 9-bromo-6-methyl-4-oxo-6,7,8,9-tetrahydro-4H-pyrido(1,2-a)pyrimidine-3-carboxylic acid are added whereafter to the suspension 155 ml. of a 50 weight/volume % aqueous hydrazine hydrate solution are rapidly poured at once under stirring. The reaction mixture warms up and a solution is formed. The reaction mixture is stirred at room temperature for 2–3 hours, whereupon the precipitated crystals are filtered off.

The filtered hydrazinium salt is dissolved in 400 ml. of water and the acid is set free by adding an equivalent amount of solid potassium bisulfate The precipitated crystals are filtered off, washed with a small amount of water and dried. After recrystallization from 50% aqueous ethanol 40.2 g. (60.8%) of 9-hydrazono-6-methyl-4-oxo-6,7,8,9-tetrahydro-4H-pyrido(1,2-a)pyrimidine-3-carboxylic acid are obtained. M.P.: 202°–203° C.

Analysis for the formula $C_{10}H_{12}N_4O_3$: Calculated: C: 50.84%; H: 5.12%; N: 23.72%; Found: C: 50.46:%; H: 5.30%; N: 23.68%.

EXAMPLE 27

Into a suspension of 34.0 g. (0.14 mole) of 9-hydrazono-6-methyl-4-oxo-6,7,8,9-tetrahydro-4H-pyrido(1,2-a)pyrimidine-3-carboxylic acid and 700 ml. of anhydrous ethanol dry gaseous hydrogen chloride is introduced at 10°–15° C. under stirring. After saturation took place the solution is allowed to stand in a refrigerator overnight.

Next day the solvent is distilled off in vacuo. The residue is dissolved in 50 ml of water, the solution obtained is neutralized with a 5 weight/volume % aqueous sodium carbonate solution and extracted four times with 100 ml. of chloroform each. The united organic phase is dried over anhydrous sodium sulfate and evaporated in vacuo. After cyrstallization of the residue from methanol 18.0 g. (48.6%) of ethyl-9-hydrazono-6-methyl-4-oxo-6,7,8,9-tetrahydro-4H-pyrido(1,2-a)pyrimidine-3-carboxylate are obtained. mp, 199°–200° C.

Analysis for the formula $C_{12}H_{16}N_4O_3$: Calculated: C: 54.54%; H: 6.10%; N: 21.20%; Found: C: 53.88%; H: 6.20%; N: 21.10%.

EXAMPLE 28

To a solution of 2.0 g. (7.57 millimoles) of ethyl-9-hydrazono-6-methyl-4-oxo-6,7,8,9-tetrahydro-4H-pyrido(1,2-a)pyrimidine-3-carboxylate and 20 ml. of anhydrous chloroform 1.6 ml. (11.35 millimoles) of triethylamine and 1.3 ml. (11.35 millimoles) of benzoyl chloride are added. The mixture is heated to boiling for 2 hours, whereupon it is cooled to room temperature and thoroughly admixed with 20 ml. of water. The organic phase is separated and the aqueous layer is extracted with 10 ml. of chloroform. The united organic phase is dried over anhydrous sodium sulfate and evaporated in vacuo. The residue is recrystallized from methanol. Thus 1.5 g. (53.8%) of ethyl-9-(benzoyl-hydrazono)-6-methyl-4-oxo-6,7,8,9-tetrahydro-4H-pyrido(1,2-a)pyrimidine-3-carboxylate are obtained. Mp.: 209°–210° C.

Analysis for the formula $C_{19}H_{20}N_4O_4$: Calculated: C: 61.96%; H: 5.47%; N: 15.20%; Found: C: 62.02%; H: 5.58%; N: 15.61%;

EXAMPLE 29

A suspension of 2.0 g. (7.57 millimoles) of ethyl-9-hydrazono-6-methyl-4-oxo-6,7,8,9-tetrahydro-4H-pyrido(1,2-a)pyrimidine-3-carboxylate and 20 ml. of ethanol is heated to boiling whereupon 4.0 ml. of a 50 weight/volume % aqueous hydrazine hydrate solution is added dropwise. The reaction mixture is heated to boiling for 15 minutes, whereby a solution is formed. On cooling crystallization takes place.

On recrystallization of the crude product from methanol 1.0 g. (52.8%) of 9-hydrazono-6-methyl-4-oxo-6,7,8,9-tetrahydro-4H-pyrido(1,2-a)pyrimidine-3-carbohydrazide are obtained. Mp.: 219°-220° C.

Analysis for the formula $C_{10}H_{14}N_6O_2$: Calculated: C: 47.99%; H: 5.64%; N: 33.58%; Found: C: 48.43%; H: 5.67%; N: 23.59%.

EXAMPLE 30

To a solution of 4.0 g. (12.73 millimoles) of ethyl-9-bromo-6-methyl-4-oxo-6,7,8,9-tetrahydro-4H-pyrido(1,2-a)pyrimidine-3-carboxylate and 20 ml. of ethanol 8.0 ml. of a 50 weight/volume % aqueous hydrazine-hydrate solution are added dropwise under stirring. The solution is stirred at room temperature for 2 hours. The precipitated crystals are filtered off, washed with a small amount of ethanol and dried. On recrystallization from ethanol 1.6 g. (50.2%) of 9-hydrazono-6-methyl-4-oxo-6,7,8,9-tetrahydro-4H-pyrido(1,2-a)pyrimidine-3-carbohydrazide are obtained. Mp.: 219°-220° C. The product does not show a melting point depression when admixed with the compound prepared according to Example 29.

EXAMPLE 31

10.0 g. (0.03 moles) of ethyl-9-(phenyl-hydrazono)-6-methyl-4-oxo-6,7,8,9-tetrahydro-4H-pyrido(1,2-a)pyrimidine-3-carboxylate are dissolved in 30 ml. of ethanol under warming. To the solution 40 ml. of a concentrated aqueous ammonium hydroxide solution are added under stirring. The reaction mixture is allowed to stand for a day, then the precipitated crystals are filtered off.

On recrystallizing the crude product from nitromethane 5.0 g. (53.5%) of 9-(phenyl-hydrazono)-6-methyl-4-oxo-6,7,8,9-tetrahydro-4H-pyrido(1,2-a)pyrimidine-3-carboxamide are obtained. Mp.: 246°-247° C.

Analysis for the formula $C_{16}H_{17}N_5O_2$: Calculated: C: 61.73%; H: 5.50%; N: 22.49%; Found: C: 61.51%; H: 5.58%; N: 23.17%.

EXAMPLE 32

One proceeds as described in Example 6 except that instead of an aqueous solution of ethyl-6-methyl-4-oxo-6,7,8,9-tetrahydro-4H-pyrido(1,2-a)pyrimidine-3-carboxylate an acetone solution of 6-methyl-4-oxo-6,7,8,9-tetrahydro-4H-pyrido(1,2-a)pyrimidine-3-carbonitrile is added dropwise to the reaction mixture. The melting point of the 9-(phenyl-hydrazono)-6-methyl-4-oxo-6,7,8,9-tetrahydro-4H-pyrido(1,2-a)pyrimidine-3-carbonitrile-monohydrate thus obtained amounts to 223°-224° C.

Analysis for the formula $C_{16}H_{15}N_5O.H_2O$: Calculated: C: 61.73%; H: 5.50%; N: 22.49%; Found: C: 61.40%; H: 5.32%; N: 22.76%:

EXAMPLE 33

To a mixture of 0.9 g. (0.01 mole) of aniline and 5 ml. of a 1:1 diluted aqueous hydrochloric acid solution at 0°-5° C. under stirring a solution of 0.7 g. (0.01 mole) of of sodium nitrite and 5 ml. of water is slowly added dropwise. To the reaction mixture 6.0 g. of solid sodium acetate are added in portions, whereupon a solution of 2.5 g. (0.01 mole) of ethyl-9-formyl-6-methyl-4-oxo-1,6,7,8-tetrahydro-4H-pyrido(1,2-a)pyrimidine-3-carboxylate and 20 ml. of acetone is added under vigorous stirring.

The reaction mixture is stirred at 0°-5° C. for 3-4 hours, whereupon the acetone is distilled off in vacuo. The residual aqueous solution is extracted three times with 10 ml. of chloroform each. The united organic phases are thoroughly admixed with 30 ml. of water, the layers are separated, the chloroform solution is dried over anhydrous sodium sulfate and evaporated in vacuo. The residue is recrystallized from ethanol, the crystals are dried at 90°-100° C. over phosphorous pentoxide in a vacuum-drier. Thus 0.7 g. (20.6%) of ethyl-9-(phenyl-hydrazono)-6-methyl-4-oxo-6,7,8,9-tetrahydro-4H-pyrido(1,2-a)pyrimidine-3-carboxylate is obtained, which melts at 138°-139° C. and does not give any melting point depression when admixed with the compound prepared according to Example 1, 2 or 3.

EXAMPLE 34

To 12 ml. of dimethylsulfoxide 2.0 g. (7.57 millimoles) of ethyl-9-hydrazono-6-methyl-4-oxo-6,7,8,9-tetrahydro-4H-pyrido(1,2-a)pyrimidine-3-carboxylate are added. To the suspension 1.2 ml. (11.88 millimoles) of benzaldehyde are added. The reaction mixture is allowed to stand at room temperature for 4-6 days, whereby a solution is obtained. The solution is diluted with 20 ml. of water and extracted three times with 30 ml. of benzene each. The united organic layer is dried over anhydrous sodium sulfate and evaporated in vacuo. To the residual dark oil 25 ml. of diethyl ether are added, whereby crystals precipitate. The crystals are filtered off and washed with a small amount of ether. Yield: 2.0 g. (75.0%). The end-product is a mixture of isomers. The isomers are separated on a preparative plate prepared with a Kieselgel 60 $PF_{254+366}$ absorbent (20×20 cm., thickness 1.5 mm.) by thin layer chromatography. Developing agent: 7:1 mixture of benzene and methanol. Eluent: 1:10 mixture of methanol and dichloromethane. The product having a higher $R_F$ value is the ethyl-9-(benzylidene-hydrazino)-6-methyl-4-oxo-6,7-dihydro-4H-pyrido(1,2-a)pyrimidine-3-carboxylate, mp.: 142°-144° C.

Analysis for the formula $C_{19}H_{20}N_4O_3$: Calculated: C: 64.77%; H: 5.72%; N: 15.89%; Found: C: 64.70%; H: 5.85%; N: 15.73%.

The product having a lower $R_F$ value is the ethyl-9-(benzylidene-hydrazono)-6-methyl-4-oxo-6,7,8,9-tetrahydro-4H-pyrido(1,2-a)pyrimidine-3-carboxylate, m.p.: 133°-134° C., yield: 0.75 g.

Analysis for the formula $C_{19}H_{20}N_4O_3$: Calculated: C: 64.77%; H: 5.72%; N: 15.89%; Found: C: 64.43%; H: 5.53%; N: 15.82%.

EXAMPLE 35

One proceeds as described in Example 14 except that aniline is replaced by p-phenetidine. Thus 9-(p-ethoxyphenyl-hydrazono)-6-methyl-4-oxo-6,7,8,9-tetrahydro-4H-pyrido(1,2-a)pyrimidine-3-carboxylic acid are obtained. Yield: 7.6 g. (53.3%). Mp.: 218°-219° C.

Analysis for the formula $C_{18}H_{20}N_4O_4$: Calculated: C: 60.67%; H: ;b 5.66%; N: 15.72%; Found: C: 60.52%; H: 5.73%; N: 15.74%.

EXAMPLE 36

One proceeds as described in Example 14 except that 6-methyl-4-oxo-6,7,8,9-tetrahydro-4H-pyrido(1,2-a)pyrimidine-3-carboxylic acid is replaced by (−)-6-methyl-4-oxo-6,7,8,9-tetrahydro-4H-pyrido(1,2-a)pyrimidine-3-carboxylic acid $\{[\alpha]_D^{20}=-113.7°$ (C=2, methanol)$\}$. Thus (−)-9-(phenylhydrazono)-6- methyl-4-oxo-6,7,8,9-tetrahydro-4H-pyrido (1,2-a)pyrimidine-3-carboxylic acid is obtained. Mp.: 258°–259° C. $[\alpha]_D^{20} = -407.5°$ (C=2, dimethylformamide). Yield: 91.0%.

Analysis for the formula $C_{16}H_{16}N_4O_3$: Calculated: C: 61.53%; H: 5.16%; N: 17.94%; Found: C: 61.48%; H: 5.04%; N: 17.82%.

EXAMPLE 37

One proceeds as described in Example 14 except that 6-methyl-4-oxo-6,7,8,9-tetrahydro-4H-pyrido(1,2-a)pyrimidine-3-carboxylic acid is replaced by (+)-6-methyl-4-oxo-6,7,8,9-tetrahydro-4H-pyrido(1,2-a)pyrimidine-3-carboxylic acid $\{[\alpha]_D^{20} = +110°$ (C=2, methanol)$\}$. Thus (+)-9-(phenylhydrazono)-6-methyl-4-oxo-6,7,8,9-tetrahydro-4H-pyrido(1,2-a)pyrimidine-3-carboxylic acid is obtained $\{[\alpha]_D^{20} = = +407.5°$ (C=2, dimethylformamide)$\}$, mp.: 255°–256° C. Yield: 92.5%.

Analysis for the formula $C_{16}H_{16}N_4O_3$: Calculated: C: 61.53%; H: 5.16%; N: 17.94%; Found: C: 61.72%; H: 5.22%; N: 18.01%.

EXAMPLE 38

One proceeds as described in Example 1 except that 6-methyl-4-oxo-6,7,8,9-tetrahydro-4H-pyrido(1,2-a)pyrimidine-3-carboxylic acid is replaced by 7-methyl-4-oxo-6,7,8,9-tetrahydro-4H-pyrido(1,2-a)pyrimidine-3-carboxylic acid. Thus 9-(phenyl-hydrazono)-7-methyl-4-oxo-6,7,8,9-tetrahydro-4H-pyrido(1,2-a)pyrimidine-3-carboxylic acid is obtained. Mp: 255°–256° C.

Analysis for the formula $C_{16}H_{16}N_4O_3$: Calculated: C: 61.53%; H: 5.16%; N: 17.94%; Found: C: 61.27%; H: 5.17%; N: 17.78%.

EXAMPLES 39-62

0.03 mole of an aniline derivative disclosed in Table I is dissolved in 14.4 ml. of 18 weight/volume % hydrochloric acid, the solution is cooled to 0°–5° C. and at this temperature a solution of 2.1 g. of sodium nitrite and 15 ml. of water is added dropwise. To the reaction mixture 18 g. of sodium acetate are added and to the diazonium salt solution thus formed a mixture of 0.03 mole of 6-methyl-4-oxo-6,7,8,9-tetrahydro-4H-pyrido(1,2-a)pyrimidine-3-carboxylic acid in an aqueous solution of 30 ml. of water and 7 ml. of 10 weight/volume % sodium hydroxide is added dropwise at a temperature below 5° C. The addition having been completed the reaction mixture is stirred at 0°–5° C. and the precipitated crystals are filtered off and washed with water. The product is crystallized from the solvent disclosed in Table I.

EXAMPLE 63

7.8 g. (0.02 mole) of ethyl-9-(phenyl-hydrazono)-6-methyl-4-oxo-6,7,8,9-tetrahydro-4H-pyrido(1,2-a)pyrimidine-3-carboxylate are dissolved in 100 ml. of ethanol. To the solution 6.0 ml. of 98% hydrazine-hydrate are added and the reaction mixture is refluxed for 2 hours. On cooling the precipitation of crystals begins. The crystals are filtered off and washed with ethanol. Thus 5.4 g. (82.7%) of 9-(phenyl-hydrazono)-6-methyl-4-oxo-6,7,8,9-tetrahydro-4H-prido(1,2-a)pyrimidine-3-carbohydrazide are obtained. Mp.: 205°–207° C.

Analysis for the formula $C_{16}H_{18}N_6O_2$: Calculated: C: 58.89%; H: 5.56%; N: 25.75%; Found: C: 59.06%; H: 5.47%; N: 25.52%.

EXAMPLE 64

In 150 ml. of methanol 10.0 g. (34.95 millimoles) of 9-bromo-6-methyl-4-oxo-6,7,8,9-tetrahydro-4H-pyrido(1,2-a)pyrimidine-3-carboxamide are dissolved under heating. To the solution 20 ml. hydrazine hydrate are added dropwise under stirring carefully within 10 minutes. The reaction mixture is heated to boiling for 40 minutes whereupon the methanol is distilled off in vacuo. The crystals are filtered off, washed with water and crystallized from water. Thus 3.8 g. (46.5%) of 9-hydrazono-6-methyl-4-oxo-6,7,8,9-tetrahydro-4H-pyrido(1,2-a)pyrimidine-3-carboxamide are obtained. Mp.: 248°–250° C.

Analysis for the formula $C_{10}H_{13}N_5O_2$: Calcuated: C: 51.06%; H: 5.57%; N: 29.77%; Found: C: 50.59%; H: 5.46%; N: 29.85%.

EXAMPLES 65-67

2.9 g. of (0.01 mole) of 9-bromo-6-methyl-4-oxo-6,7,8,9-tetrahydro-4H-pyrido(1,2-a)pyrimidine-3-carboxamide are dissolved in 20 ml. of methaol and 0.025 mole of a hydrazine derivative enumerated in Table II is added. The reaction mixture is stirred for 1–3 hours at the boiling point. The product is filtered off or isolated by evaporation. The product may be recrystallized from water.

EXAMPLES 68-69

2.9 g. (0.01 mole) of 9-bromo-6-methyl-4-oxo-6,7,8,9-tetrahydro-4H-pyrido(1,2-a)pyrimidine-3-carboxylic acid are dissolved in 20 ml. of methanol and 0.025 mole of a hydrazine derivative enumerated in Table III are added. The reaction mixture is heated to boiling for 1–3 hours. The product is either filtered off or isolated by evaporation and may be recrystallized from water.

EXAMPLE 70

The compound 9-(phenyl-hydrazono)-6-methyl-4-oxo-6,7,8,9-tetrahydro-4H-pyrido(1,2-a)pyrimidine-3-carboxylic acid is prepared by the process disclosed in Example 14 except that sodium acetate is added to the reaction mixture. Yield: 75%. Mp.: 256°–57° C. The product does not show a melting point depression when admixed with the compounds prepared according to Example 14.

Analysis for the formula $C_{16}H_{16}N_4O_3$: Calculated: C: 61.53%; H: 5.16%; N: 17.94%; Found: C: 61.48%; H: 5.01%; N: 17.80%.

EXAMPLE 71

The process according to Example 6 is carried out except that p-chloro-aniline is replaced by aniline and ethyl-6-methyl-4-oxo-6,7,8,9-tetrahydro-4H-pyrido(1,2-a)pyrimidine-3-carboxylate is replaced by ethyl-7-methyl-4-oxo-6,7,8,9-tetrahydro-4H-pyrido(1,2-a)pyrimidine-3-carboxylate, respectively. Thus ethyl-9-(phenyl-hydrazono)-7-methyl-4-oxo-6,7,8,9-tetrahydro-4H-pyrido(1,2-a)pyrimidine-3-carboxylate is obtained with a yield of 60.2%. Mp.: 165°–167° C.

Analysis for the formula $C_{18}H_{20}N_4O_3$: Calculated: C: 63.51%; H: 5.92%; N: 16.45%; Found: C: 63.24%; H: 5.80%; N: 16.35%.

EXAMPLE 72

The process according to Example 6 is carried out with the difference that aniline and ethyl-8-methyl-4-oxo-6,7,8,9-tetrahydro-4H-pyrido(1,2-a)pyrimidine-3- carboxylate are used as starting material. Thus ethyl-9-(phenyl-hydrazono)-8-methyl-4-oxo-6,7,8,9-tetrahydro-4H-pyrido(1,2-a)pyrimidine-3-carboxylate is obtained with a yield of 61.5%. Mp.: 108°–110° C.

Analysis for the formula $C_{18}H_{20}N_4O_3$: Calculated: C: 63.51%; H: 5.92%; N: 16.45%; Found: C: 63.30%; H: 6.01%; N: 16.52%.

EXAMPLE 73

The process according to Example 6 is carried out with the difference that aniline and dimethylformamide solution of 2,6-dimethyl-4-oxo-6,7,8,9-tetrahydro-4H-pyrido(1,2-a)pyrimidine-3-carboxamide is used. The crude 9-(phenyl-hydrazono)-2,6-dimethyl-4-oxo-6,7,8,9-tetrahydro-4H-pyrido(1,2-a)pyrimidine-3-carboxamide melts at 235°–237° C., yield: 49.2%.

Analysis for the formula $C_{17}H_{19}N_5O_2$: Calculated: C: 62.76%; H: 5.89%; N: 21.52%; Found: C: 62.84%; H: 5.77%; N: 21.51%.

EXAMPLE 74

5.7 g (0.02 moles) of 9-bromo-6-methyl-4-oxo-6,7,8,9-tetrahydro-4H-pyrido(1,2-a)pyrimidine-3-carboxylic acid are dissolved in 30 ml of anhydrous ethanol, whereupon 4.3 ml (0.044 moles) of phenyl-hydrazine are added. The reaction mixture is refluxed for 4 hours under stirring, whereupon the precipitated crystals are filtered off and washed with ethanol. Thus 4.7 g (75.2%) of 9-phenyl-hydrazono)-6-methyl-4-oxo-6,8,8,9-tetrahydro-4H-pyrido-(1,2-a)pyrimidine-3-carboxylic acid are obtained. Mp.: 258°–260° C. After recrystallization from dimethyl-formamide the melting point rises to 267°–268° C. The product does not give a melting point depression when admixed with the product prepared according to Example 14.

EXAMPLE 75

2.2 g (0.01 mole) of 9-hydroxy-6-methyl-4-oxo-6,7-dihydro-4H-pyrido(1,20a)pyrimidine-3-carboxylic acid are dissolved in 15 ml of anhydrous ethanol. To the solution 1.2 ml (0.012 mole) of phenyl-hydrazine are added. The reaction mixture is refluxed for half an hour under stirring. The precipitated crystals are filtered off and washed with ethanol. Thus 2.4 g (76%) of 9-phenyl-hydrazono)-6-methyl-4-oxo-6,7,8,9-tetrahydro-4H-pyrido(1,2-a)pyrimidine-3-carboxylic acid are obtained. Mp.: 267°–268° C. (from dimethylformamide). No melting point depression with the product according to Example 14.

EXAMPLE 76

One proceeds according to Example 74 except that (+)-9-bromo-6-methyl-4-oxo-6,7,8,9-tetrahydro-4H-pyrido(1,2-a)-pyrimidine-3-carboxylic acid $\{[\alpha]_D^{20}=-45°$ [c=1, methaol]} is used. Thus (+)-9-(phenyl-hydrazono)-6-methyl-4-oxo-6,7,8,9-tetrahydro-4H-pyrido(1,2-a)pyrimidine-3-carboxylic acid is obtained. The product is identical with the compound prepared according to Example 37 and gives with the same no melting point depression. Yield: 76.0%.

Mp.: 256°–7° C.; $[\alpha]_D^{20}=+407.5°$ [c=2, dimethylformamide].

EXAMPLE 77

To a mixture of 0.45 ml (0.005 mole) of aniline and 2.5 ml of a 1:1 mixture of aqueous hydrochloric acid a solution of 0.3 g (0.005) moles of sodium nitrite and 2.4 ml of water is slowly added at 0°–5° C. To the reaction mixture 3.0 ml of solid sodium acetate are added whereupon a solution of 1.2 g (0.005 mole) of ethyl-(6-methyl-4-oxo-6,7,8,9-tetrahydro-4H-pyrido)1,2-a(pyrimidine-3-yl)-acetate and 2.5 ml of water is slowly added under vigorous stirring. The reaction mixture is stirred at 0°–5° C. for 2–3 hours whereupon it is allowed to stand in a refrigerator overnight. The aqueous phase is decanted and the residual yellowish gum is recrystallized fro methanol. Thus 0.5 g (25.9%) of ethyl-[9-(phenyl-hydrazono)-6-methyl-4-oxo-6,7,8,9-tetrahydro-4H-pyrido-(1,2-a)pyrimidine-3-yl]-acetate are obtained. The product contains 1 molequivalent of crystal methanol. Mp.: 100°–102° C.

Analysis: for the Formula $C_{19}H_{22}N_4O_3 \cdot CH_3OH$: Calculated C: 62.16%; H: 6.78%; N: 14.50%; Found C: 62.34%; H: 6.69%; N: 14.73%;

EXAMPLE 78

One proceeds according to Example 77 except that (6-methyl-4-oxo-6,7,8,9-tetrahydro-4H-pyrido(1,2-a)pyrimidine-3-yl)-acetic acid is used as starting material. The crude product obtained is diluted with a tenfold amount of water, the pH is adjusted to the value of 8 with sodium hydroxide solution, whereupon the solution formed is acidified to pH=3 with hydrochloric acid. The precipitated crystals are filtered off and washed with water. Thus [9-(phenyl-hydrazono)-6-methyl-4-oxo-6,7,8,9-tetrahydro-4H-pyrido(1,2-a)pyrimidine-3-yl]-acetic acid is obtained. Yield: 59.5%. Mp.: 160°–2° C.

Analysis: for the formula $C_{17}H_{18}N_4O_3$: calculated C: 62.57%; H: 5.56%; N: 17.17%; found: C: 63.11%; H: 5.49%; N: 16.98%.

EXAMPLE 79

One proceeds according to Example 77 except that 6-methyl-6,7,8,9-tetrahydro-4H-pyrido(1,2-a)pyrimidine-4-one is used as starting material. Thus 9-(phenyl-hydrazono)-6-methyl-6,7,8,9-tetrahydro-4H-pyrido(1,2-a)pyrimidine-4-one is obtained. Yield: 52.2%. Mp.: 163°–165° C.

Analysis: for the formula $C_{15}H_{16}N_4O$: calculated C: 67.15%; H: 6.01%; N: 20.88%; found C: 66.92%; H: 5.98%; N: 21.00%.

EXAMPLES 80–87

The following compounds of formula I enumerated in Table IV are prepared according to the process described in Examples 39–62.

TABLE I

| No. | Aniline starting material | Product obtained | Yield % | Mp. °C | Recryst. solvent | Empirical formula | Analysis (%) Calc. C | H | Found N |
|---|---|---|---|---|---|---|---|---|---|
| 39 | 2-fluoro-aniline | 9-(2-fluoro-phenyl-hydrazono)-6-methyl-4-oxo-6,7,8,9-tetra-hydro-4H—pyrido(1,2-a)pyrimi-dine-3-carboxylic acid | 65 | 216–17 | methanol[a] | $C_{16}H_{15}N_4O_3F$ | 58.18 58.03 | 4.58 4.60 | 16.96 16.76 |
| 40 | 2,4-di- | 9-(2,4-dichloro-phenyl- | 79 | 242–44 | DMF | $C_{16}H_{14}N_4O_3Cl_2$ | 50.41 | 3.70 | 14.70 |

TABLE I-continued

| No. | Aniline starting material | Product obtained | Yield % | Mp. °C. | Recryst. solvent | Empirical formula | Calc. C | Calc. H | Found N |
|---|---|---|---|---|---|---|---|---|---|
| | chloroaniline | hydrazono)-6-methyl-4-oxo-6,7,8,9-tetrahydro-4H—pyrido-(1,2-a)pyrimidine-3-carboxylic acid | | | | | 50.62 | 3.69 | 14.86 |
| 41 | 3,4-dichloroaniline | 9-(3,4-dichloro-phenyl-hydrazono)-6-methyl-4-oxo-6,7,8,9-tetrahydro-4H—pyrido-(1,2-a)pyrimidine-3-carboxylic acid | 90.5 | 248–50 | acetic acid | $C_{16}H_{14}N_4O_3Cl_2$ | 50.41 50.62 | 3.70 3.70 | 14.70 14.65 |
| 42 | o-aminophenol | 9-(2-hydroxy-phenyl-hydrazono)-6-methyl-4-oxo-6,7,8,9-tetrahydro-4H—pyrido(1,2-a)pyrimidine-3-carboxylic acid | 44 | 252–54 | DMF | $C_{16}H_{16}N_4O_4$ | 59.03 58.80 | 4.85 4.69 | 16.86 17.00 |
| 43 | 3-nitroaniline | 9-(3-nitro-phenyl)-hydrazono-6-methyl-4-oxo-6,7,8,9-tetrahydro-4H—pyrido(1,2-a)pyrimidine-3-carboxylic acid | 67.2 | 268–70 | DMF:acetic acid 2:1 | $C_{16}H_{15}N_5O_5$ | 53.78 53.26 | 4.23 4.22 | 19.60 19.62 |
| 44 | o-nitroaniline | 9-(2-nitro-phenyl)-hydrazono-6-methyl-4-oxo-6,7,8,9-tetrahydro-4H—pyrido(1,2-a)pyrimidine-3-carboxylic acid | 65.8 | 270–74 | methanol[a] | $C_{16}H_{15}N_5O_5$ | 53.78 53.27 | 4.23 4.18 | 19.60 19.70 |
| 45 | m-chloroaniline | 9-(3-chloro-phenyl-hydrazono)-6-methyl-4-oxo-6,7,8,9-tetrahydro-4H—pyrido(1,2-a)pyrimidine-3-carboxylic acid | 64.9 | 263–65 | acetic acid | $C_{16}H_{15}N_4O_3Cl$ | 55.42 55.27 | 4.36 4.09 | 16.16 16.06 |
| 46 | p-iodoaniline | 9-(4-iodo-phenyl-hydrazono)-6-methyl-4-oxo-6,7,8,9-tetrahydro-4H—pyrido(1,2-a)pyrimidine-3-carboxylic acid | 70.7 | 245–46 | ethanol[a] | $C_{16}H_{15}N_4O_3I$ | 43.85 43.46 | 3.45 3.30 | 12.78 12.79 |
| 47 | 1-naphthylamine | 9-(1-naphthyl-hydrazono)-6-methyl-4-oxo-6,7,8,9-tetrahydro-4H—pyrido(1,2-a)pyrimidine-3-carboxylic acid | 63.5 | 240–42 | acetic acid | $C_{20}H_{18}N_4O_3$ | 66.29 66.10 | 5.01 5.23 | 15.46 15.26 |
| 48 | p-aminobenzoic acid | 9-(4-carboxy-phenyl-hydrazono)-6-methyl-4-oxo-6,7,8,9-tetrahydro-4H—pyrido(1,2-a)pyrimidine-3-carboxylic acid | 84.2 | 280–81 | methanol[a] | $C_{17}H_{16}N_4O_5$ | 57.30 57.50 | 4.52 4.42 | 15.72 15.53 |
| 49 | 2-chloro-6-methylaniline | 9-(2-methyl-6-chloro-phenyl)-hydrazono)-6-methyl-4-oxo-6,7,8,9-tetrahydro-4H—pyrido-(1,2-a)pyrimidine-3-carboxylic acid | 94 | 205–07 | acetic acid | $C_{17}H_{17}N_4O_3Cl$ | 56.59 56.34 | 4.75 4.53 | 15.52 15.41 |
| 50 | m-toluidine | 9-(3-methyl-phenyl-hydrazono)-6-methyl-4-oxo-6,7,8,9-tetrahydro-4H—pyrido(1,2-a)pyrimidine-3-carboxylic acid | 88 | 242–44 | methanol[a] | $C_{17}H_{18}N_4O_3$ | 62.57 62.60 | 5.56 5.46 | 17.17 17.27 |
| 51 | α,α,α-trifluoro-o-toluidine | 9-(2-trifluoromethyl-phenyl-hydrazono)-6-methyl-4-oxo-6,7,8,9-tetrahydro-4H—pyrido(1,2-a)pyrimidine-3-carboxylic acid | 80 | 268–69 | acetic | $C_{17}H_{15}N_4O_3F_3$ | 53.69 53.76 | 3.98 3.80 | 14.73 14.76 |
| 52 | α,α,α-trifluoro-m-toluidine | 9-(3-trifluoromethyl)-phenyl-hydrazono)-6-methyl-4-oxo-6,7,8,9-tetrahydro-4H—pyrido(1,2-a)pyrimidine-3-carboxylic acid | 93 | 273–74 | methanol[a] | $C_{17}H_{15}N_4O_3F_3$ | 53.69 53.72 | 3.98 3.80 | 14.73 14.62 |
| 53 | 2,6-diethylaniline | 9-(2,6-diethyl-phenyl-hydrazono)-6-methyl-4-oxo-6,7,8,9-tetrahydro-4H—pyrido(1,2-a)pyrimidine-3-carboxylic acid | 23 | 160–63 | benzene | $C_{20}H_{24}N_4O_3$ | 65.20 65.13 | 6.57 6.63 | 15.21 15.30 |
| 54 | p-fluoroaniline | 9-(4-fluoro-phenyl-hydrazono)-6-methyl-4-oxo-6,7,8,9-tetrahydro-4H—pyrido(1,2-a)pyrimidine-3-carboxylic acid | 90 | 246–48 | methanol[a] | $C_{16}H_{15}N_4O_3F$ | 58.18 58.00 | 4.58 4.45 | 16.96 16.86 |
| 55 | p-toluidine | 9-(4-methyl-phenyl-hydrazono)-6-methyl-4-oxo-6,7,8,9-tetrahydro-4H—pyrido(1,2-a)pyrimidine-3-carboxylic acid | 85 | 242–44 | acetic acid | $C_{17}H_{18}N_4O_3$ | 62.57 62.41 | 5.56 5.49 | 17.17 16.99 |
| 56 | 2,6-dichloroaniline | 9-(2,6-dichloro-phenyl-hydrazono)-6-methyl-4-oxo-6,7,8,9-tetrahydro-4H—pyrido-(1,2-a)pyrimidine-3-carboxylic acid | 56 | 230–32 | acetic acid | $C_{16}H_{14}N_4O_3Cl_2$ | 50.41 50.89 | 3.70 3.58 | 14.70 14.78 |
| 57 | p-aminophenol | 9-(4-hydroxy-phenyl-hydrazono)-6-methyl-4-oxo-6,7,8,9-tetrahydro-4H—pyrido(1,2-a)pyrimidine-3-carboxylic acid | 82 | 240–42 | acetic acid | $C_{16}H_{16}N_4O_4$ | 59.03 59.08 | 4.85 4.85 | 16.86 17.00 |

TABLE I-continued

| No. | Aniline starting material | Product obtained | Yield % | Mp. °C. | Recryst. solvent | Empirical formula | Analysis (%) Calc. C / H / Found N |
|---|---|---|---|---|---|---|---|
| 58 | 3,4-methylen-dioxy-aniline | 9-(3,4-methylendioxy-phenyl-hydrazono)-6-methyl-4-oxo-6,7,8,9-tetrahydro-4H—pyrido-(1,2-a)pyrimidine-3-carboxylic acid monohydrate | 81 | 226–27 | acetic acid | $C_{17}H_{18}N_4O_6$ | 54.54 4.85 14.97 / 54.21 4.88 15.00 |
| 59 | 4-bromo-2-chloro-aniline | 9-(4-bromo-2-chloro-phenyl-hydrazono)-6-methyl-4-oxo-6,7,8,9-tetrahydro-4H—pyrido-(1,2-a)pyrimidine-3-carboxylic acid | 88 | 245–47 | acetic acid | $C_{16}H_{14}N_4O_3BrCl$ | 45.15 3.31 13.16 / 45.29 3.31 13.20 |
| 60 | p-amoni-acetofenon | 9-(4-acetyl-phenyl-hydrazono)-6-methyl-4-oxo-6,7,8,9-tetrahydro-4H—pyrido(1,2-a)pyrimidine-3-carboxylic acid | 72 | 245–47 | acetic acid | $C_{18}H_{18}N_4O_4$ | 61.01 5.12 15.81 / 60.99 5.03 15.77 |
| 61 | o-methoxy-aniline | 9-(2-methoxy-phenyl-hydrazono)-6-methyl-4-oxo-6,7,8,9-tetrahydro-4H—pyrido(1,2-a)pyrimidine-3-carboxylic acid | 96 | 216–18 | acetic acid | $C_{17}H_{18}N_4O_4$ | 59.65 5.30 16.37 / 59.30 5.23 16.29 |
| 62 | p-methoxy-aniline | 9-(4-methoxy-phenyl-hydrazono)-6-methyl-4-oxo-6,7,8,9-tetrahydro-4H—pyrido(1,2-a)pyrimidine-3-carboxylic acid | 92 | 212–14 | nitro-methane | $C_{17}H_{18}N_4O_4$ | 59.64 5.30 16.37 / 59.37 5.31 16.26 |

*boiling; DMF = dimethylformamide

TABLE II

| Example No. | Hydrazine starting material | Compound obtained | Yield (%) | Mp. °C. | Empirical Formula | Analysis % Calc. C / H / Found N |
|---|---|---|---|---|---|---|
| 65 | p-(N,N—dimethyl-amino)-benzaldehyde-hydrazone | 9-[4-(N,N—dimethyl-amino)-benzylidene-hydrazono]-6-methyl-4-oxo-6,7,8,9-tetrahydro-4H—pyrido(1,2-a)pyrimidine-3-carbox-amide | | 220–22 | $C_{19}H_{22}N_6O_2$ | 62.28 6.05 22.93 / 62.12 6.00 22.87 |
| 66 | methyl-hydrazine | 9-(methyl-hydrazono)-6-methyl-4-oxo-6,7,8,9-tetrahydro-4H—pyrido-(1,2-a)pyrimidine-3-carboxamide | 40 | 228–30 | $C_{11}H_{15}N_5O_2$ | 53.00 6.06 28.09 / 52.57 6.03 28.00 |
| 67 | 2-caprolactame-hydrazone | 9-(2-azepinylidene-hydrazone)-6-methyl-4-oxo-6,7,8,9-tetra-hydro-4H—pyrido(1,2-a)pyrimidine-3-carbox-amide | 55 | 228–30 | $C_{16}H_{22}N_6O_2$ | 58.16 6.71 25.43 / 58.12 6.57 25.41 |

TABLE III

| Example No. | Hydrazine starting material | Compound obtained | Yield (%) | Mp.: °C. | Empirical Formula | Analysis (%) Calc. C / H / Found N |
|---|---|---|---|---|---|---|
| 68 | methyl-hydrazine | 9-(methyl-hydrazo-no)-6-methyl-4-oxo-6,7,8,9-tetrahydro-4H—pyrido(1,2-a)pyrimidine-3-carboxylic acid | 25 | 216–18 | $C_{11}H_{14}N_4O_3$ | 52.79 5.62 22.38 / 51.99 5.49 22.28 |
| 69 | ε-caprolactame-hydrazone | 9-(2-azepinylidene-hydrazono)-6-methyl-4-oxo-6,7,8,9-tetra-hydro-4H—pyrido-(1,2-a)pyrimidine-3-carboxylic acid | 40 | 166–70 | $C_{16}H_{21}N_5O_3$ | 57.99 6.38 21.13 / 57.82 6.29 21.10 |

TABLE IV

| Example | Starting material | End product | Yield % | Mp °C. | Recryst. solvent | Empirical Formula | Analysis calc. / found C | H | N |
|---|---|---|---|---|---|---|---|---|---|
| 80 | 4-amino-biphenyl | 9-(4-biphenyl-hydrazono)-6-methyl-4-oxo-6,7,8,9-tetrahydro-4H—pyrido(1,2-a)-pyrimidine-3-carboxylic acid | 28.3 | 160–162 | acetic acid | $C_{22}H_{20}N_4O_3$ | 68.03 / 68.24 | 5.19 / 5.23 | 14.42 / 14.28 |
| 81 | 4-phenyl-oxy-aniline | 9-(4-phenoxy-phenyl-hydrazono)-6-methyl-4-oxo-6,7,8,9-tetra-hydro-4H—pyrido(1,2-a)-pyrimidine-3-carboxylic acid | 29.7 | 220–222 | nitro-methane | $C_{22}H_{20}N_4O_4$ | 65.34 / 65.68 | 4.98 / 4.89 | 13.85 / 13.74 |
| 82 | 2-naphthyl-amine | 9-(2-naphthyl-hydrazono)-6-methyl-4-oxo-6,7,8,9-tetrahydro-4H—pyrido(1,2-a)pyrimidine-3-carboxylic acid | 47.8 | 172–174 | nitro-methane | $C_{20}H_{18}N_4O_3$ | 66.29 / 66.14 | 5.01 / 4.94 | 15.46 / 15.17 |
| 83 | 3-amino-2-naphthalene-3-carboxylic acid | 9-(2-carboxy-3-naphthyl-hydrazono)-6-methyl-4-oxo-6,7,8,9-tetrahydro-4H—pyrido(1,2-a)-pyrimidine-3-carboxylic acid | 49.8 | 260–262 | methanol$^a$ | $C_{21}H_{18}N_4O_5$ | 62.07 / 61.80 | 4.46 / 4.27 | 13.79 / 13.51 |
| 84 | 4-ethyl-aniline | 9-(4-ethyl-phenyl-hydrazono)-6-methyl-4-oxo-6,7,8,9tetrahydro-4H—pyrido(1,2-a)pyrimidine-3-carboxylic acid | 73.4 | 208–210 | methanol$^a$ | $C_{18}H_{20}N_4O_3$ | 63.52 / 63.14 | 5.92 / 5.78 | 16.46 / 16.40 |
| 85 | 4-cyano-aniline | 9-(4-cyano-phenyl-hydrazono)-6-methyl-4-oxo-6,7,8,9-tetra-hydro-4H—pyrido-(1,2-a)pyrimidine-3-carboxylic acid | 59.3 | 223–225 | nitro-methane | $C_{17}H_{15}N_5O_3$ | 60.53 / 60.76 | 4.48 / 4.44 | 20.76 / 20.40 |
| 86 | 2-amino-aceto-phenone | 9-(2-acetyl-phenyl-hydrazono)-6-methyl-4-oxo-6,7,8,9-tetrahydro-4H—pyrido-(1,2-a)pyrimidine-3-carboxylic acid | 53.6 | 245–246 | nitro-methane | $C_{18}H_{18}N_4O_4$ | 61.01 / 61.00 | 5.12 / 4.96 | 15.81 / 15.81 |
| 87 | 3-amino-aceto-phenone | 9-(3-acetyl-phenyl-hydrazono)-6-methyl-4-oxo-6,7,8,9-tetrahydro-4H—pyrido(1,2-a)pyrimidine-3-carboxylic acid | 36.7 | 238–240 | acetic acid | $C_{18}H_{18}N_4O_4$ | 61.01 / 60.98 | 5.12 / 5.13 | 15.81 / 15.71 |

$^a$heated to boiling in methanol.

EXAMPLES 88–100

The compounds enumerated in Table V have been prepared in an analogous manner to the procedures described in Examples 39–62.

TABLE V

| Example No. | Aniline component | End product | Yield % | Mp. °C. | Recryst. solvent | Mol. form. | Analysis calc. / found C | H | N |
|---|---|---|---|---|---|---|---|---|---|
| 88 | p-(tri-fluoro-methyl)-aniline | 9-[4-(trifluoromethyl)-phenyl-hydrazono-6-methyl-4-oxo-6,7,8,9-tetrahydro-4H—pyrido(1,2-a)pyrimidine-3-carboxylic acid | 75.7 | 238–40 | methanol$^b$ | $C_{17}H_{15}N_4O_3F_3$ | 53.69 / 53.54 | 3.98 / 3.79 | 14.73 / 14.66 |
| 89 | o-chloro-aniline | 9-(2-chloro-phenyl-hydrazono)-6-methyl-4-oxo-6,7,8,9-tetrahydro-4H—pyrido(1,2-a)pyrimi-dine-3-carboxylic acid | 23.1 | 260–62 | DMF | $C_{16}H_{15}N_4O_3Cl$ | 55.42 / 55.36 | 4.36 / 4.29 | 16.16 / 16.22 |
| 90 | o-bromo-aniline | 9-(2-bromo-phenyl-hydrazono)6-methyl-4-oxo-6,7,8,9-tetrahydro-4H—pyrido(1,2-a)pyrimi-dine-3-carboxylic acid | 47.0 | 265–67 | methanol$^b$ | $C_{16}H_{15}N_4O_3Br$ | 49.12 / 49.02 | 3.86 / 3.77 | 14.32 / 14.23 |
| 91 | m-bromo- | 9-(3-bromo-phenyl- | 56.2 | 260–62 | acetic | $C_{16}H_{15}N_4O_3Br$ | 49.12 | 3.86 | 14.32 |

TABLE V-continued

| Example No. | Aniline component | End product | Yield % | Mp. °C. | Recryst. solvent | Mol. form. | Analysis calc C | H | found N |
|---|---|---|---|---|---|---|---|---|---|
| | aniline | hydrazono)-6-methyl-4-oxo-6,7,8,9-tetrahydro-4H—pyrido(1,2-a)pyrimidine-3-carboxylic acid | | | acid | | 49.00 | 3.68 | 14.43 |
| 92 | o-iodo-aniline | 9-(2-iodo-phenyl-hydrazono)-6-methyl-4-oxo-6,7,8,9-tetrahydro-4H—pyrido(1,2-a)pyrimidine-3-carboxylic acid | 59.3 | 246–8 | acetic acid | $C_{16}H_{15}N_4O_3I$ | 43.85 44.11 | 3.45 3.31 | 12.78 12.78 |
| 93 | m-iodo-aniline | 9-(3-iodo-phenyl-hydrazono)-6-methyl-4-oxo-6,7,8,9-tetrahydro-4H—pyrido(1,2-a)pyrimidine-3-carboxylic acid | 22.8 | 258–60 | acetic acid | $C_{16}H_{15}N_4O_3I$ | 43.85 43.56 | 3.45 3.28 | 12.78 12.61 |
| 94 | m-amino-benzoic acid | 9-(3-carboxy-phenyl-hydrazono)-6-methyl-4-oxo-6,7,8,9-tetrahydro-4H—pyrido(1,2-a)pyrimidine-3-carboxylic acid | 50.5 | 263–5 | methanol[b] | $C_{17}H_{16}N_4O_5$ | 57.30 57.50 | 4.52 4.39 | 15.72 15.67 |
| 95 | o-phenetidine | 9-(2-ethoxy-phenyl-hydrazono)-6methyl-4-oxo-6,7,8,9-tetrahydro-4H—pyrido(1,2-a)pyrimidine-3-carboxylic acid | 64.5 | 225–7 | nitromethane | $C_{18}H_{20}N_4O_4$ | 60.67 60.55 | 5.66 5.49 | 15.72 15.67 |
| 96 | m-phenetidine | 9-(3-ethoxy-phenyl-hydrazono)-6-methyl-4-oxo-6,7,8,9-tetrahydro-4H—pyrido(1,2-a)pyrimidine-3-carboxylic acid | 47.7 | 210–1 | nitromethane | $C_{18}H_{20}N_4O_4$ | 60.67 61.00 | 5.66 5.70 | 15.72 15.74 |

| Example No. | Aniline component | End product | Yield % | Mp. °C. | $[\alpha]_D^{20}$ | Recryst. solvent | Mol. form. | Analysis calc C | H | found N |
|---|---|---|---|---|---|---|---|---|---|---|
| 97 | p-phenetidine | (+)-9-(4-ethoxy-phenyl-[a] hydrazono)6-methyl-4-oxo-6,7,8,9-tetrahydro-4H—pyrido(1,2-a)pyrimidine-3-carboxylic acid | 50.5 | 208.9 | +350° (c = 0,1 DMF) | DMF | $C_{18}H_{20}N_4O_4$ | 60.67 60.23 | 5.66 5.49 | 15.72 15.62 |
| 98 | anthranilic acid | (+)-9-(2-carboxy-phenyl-[a] hydrazono)-6-methyl-4-oxo-6,7,8,9-tetrahydro-4H—pyrido(1,2-a)pyrimidine-3-carboxylic acid | 51.2 | 260–1 | +222.5° (c = 1, DMF) | DMF | $C_{17}H_{16}N_4O_5$ | 57.30 57.61 | 4.52 4.55 | 15.72 15.70 |
| 99 | anthranilic acid | (−)-9-(2-carboxy-phenyl-[a] hydrazono)-6-methyl-4-oxo-6,7,8,9-tetrahydro-4H—pyrido(1,2-a)pyrimidine-3-carboxylic acid | 45.6 | 261–2 | −247.5° | DMF | $C_{17}H_{16}N_4O_5$ | 57.30 57.15 | 4.52 4.44 | 15.72 15.69 |
| 100 | p-chloro-aniline | (+)-9-(4-chloro-phenyl-[a] hydrazono)-6-methyl-4-oxo-6,7,8,9-tetrahydro-4H—pyrido(1,2-a)pyrimidine-3-carboxylic acid | 59.1 | 255–6 | +190° (c = 1, DMF) | methanol[b] | $C_{16}H_{15}N_4O_3Cl$ | 55.42 55.33 | 4.36 4.21 | 16.16 16.10 |

[a] the dextro rotatory and laevo-rotatory compounds were prepared by using (+)- or (−)-6-methyl-4-oxo-6,7,8,9-tetrahydro-4H—pyrido(1,2-a)pyrimidine-3-carboxylic acid respectively.
[b] heated to boiling in methanol.

We claim:
1. A compound of the formula:

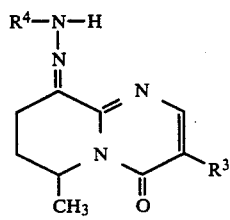

or a pharmaceutically acceptable salt, hydrate, stereoisomer, optically active isomer, geometric isomer or tautometric form thereof, wherein:
$R^3$ is hydrogen, carboxyl, lower alkoxycarbonyl, or a group of the formula $(-CH_2)_m-COOH$ or $-(CH_2)_m-COO-$lower alkyl wherein m is 1, 2 or 3; and
$R^4$ is phenyl, 4-phenyl-phenyl, 4-phenoxy-phenyl, 2-naphthyl, 3-carboxy-2-naphthyl, 4-ethyl-phenyl, 4-cyano-phenyl, 2-acetyl-phenyl, 3-acetyl-phenyl, 4-trifluoromethyl-phenyl, 2-chloropenyl, 2-bromophenyl, 3-bromo-phenyl, 2-iodo-phenyl, 3-iodophenyl, 2-carboxy-phenyl, 3-carboxy-phenyl, 2-ethoxy-phenyl or 3-ethoxy-phenyl.

2. Racemic or optically active ethyl-[9-(phenyl-hydrazono)-6-methyl-4-oxo-6,7,8,9-tetrahydro-4H-pyrido(1,2-a)pyrimidine 3-yl]-acetate as defined in claim 1.

3. Racemic or optically active 9-(phenyl-hydrazono)-6-methyl-6,7,8,9-tetrahydro-4H-pyrido(1,2a)pyrimidine-4-one as defined in claim 1.

4. Racemic or optically active [9-(phenyl-hydrazono)-6-methyl-4-oxo-6,7,8,9-tetrahydro-4H-pyrido(1,2-a)pyrimidine-3-yl]-acetic acid, as defined in claim 1.

5. Racemic or optically active 9-(4-biphenyl-hydrazono)-6-methyl-4-oxo-6,7,8,9-tetrahydro-4H-pyrido(1,2-a)pyrimidine-3-carboxylic acid as defined in claim 1.

6. Racemic or optically active 9-(4-phenoxy-phenyl-hydrazono-6-methyl-4-oxo-6,7,8,9-tetrahydro-4H-pyrido(1,2-a)pyrimidine-3-carboxylic acid as defined in claim 1.

7. Racemic or optically active 9-(2-naphthyl-hydrazono)-6-methyl-4-oxo-6,7,8,9-tetrahydro-4H- pyrido(1,2-a)pyrimidine-3-carboxylic acid as defined in claim 1.

8. Racemic or optically active 9-(3-carboxy-2-naphthyl-hydrazono)-6-methyl-4-oxo-6,7,8,9-tetrahydro-4H-pyrido(1,2-a)pyrimidine-3-carboxylic acid as defined in claim 1.

9. Racemic or optically active 9-(4-ethyl-phenyl-hydrazono)-6-methyl-4-oxo-6,7,8,9-tetrahydro-4H-pyrido(1,2-a)pyrimidine-3-carboxylic acid as defined in claim 1.

10. Racemic or optically active 9-(4-cyano-phenyl-hydrazono)-6-methyl-4-oxo-6,7,8,9-tetrahydro-4H-pyrido(1,2-a)pyrimidine-3-carboxylic acid as defined in claim 1.

11. Racemic or optically active 9-(2-acetyl-phenyl-hydrazono)-6-methyl-4-oxo-6,7,8,9-tetrahydro-4H-pyrido(1,2-a)pyrimidine-3-carboxylic acid as defined in claim 1.

12. Racemic or optically active 9-(3-acetyl-phenyl-hydrazono)-6-methyl-4-oxo-6,7,8,9-tetrahydro-4H-pyrido(1,2-a)pyrimidine-3-carboxylic acid as defined in claim 1.

13. Racemic or optically active 9-[4-trifluoromethyl)-phenyl-hydrazono]-6-methyl-4-oxo-6,7,8,9-tetrahydro-4H-pyrido(1,2-a)pyrimidine-3-carboxylic acid as defined in claim 1.

14. Racemic or optically active 9-(2-chloro-phenyl-hydrazono)-6-methyl-4-oxo-6,7,8,9-tetrahydro-4H-pyrido(1,2-a)pyrimidine-3-carboxylic acid as defined in claim 1.

15. Racemic or optically active 9-(2-bromo-phenyl-hydrazono)-6-methyl-4-oxo-6,7,8,9-tetrahydro-4H-pyrido(1,2-a)pyrimidine-3-carboxylic acid as defined in claim 1.

16. Racemic or optically active 9-(3-bromo-phenyl-hydrazono-6-methyl-4-oxo-6,7,8,9-tetrahydro-4H-pyrido(1,2-a)pyrimidine-3-carboxylic acid as defined in claim 1.

17. Racemic or optically active 9-(2-iodo-phenyl-hydrazono)-6-methyl-4-oxo-6,7,8,9-tetrahydro-4H-pyrido(1,2-a)pyrimidine-3-carboxylic acid as defined in claim 1.

18. Racemic or optically active 9-(3-iodo-phenyl-hydrazono)-6-methyl-4-oxo-6,7,8,9-tetrahydro-4H-pyrido(1,2-a)pyrimidine-3-carboxylic acid as defined in claim 1.

19. Racemic or optically active 9-(3-carboxy-phenyl-hydrazono)-6-methyl-4-oxo-6,7,8,9-tetrahydro-4H-pyrido(1,2-a)pyrimidine-3-carboxylic acid as defined in claim 1.

20. Racemic or optically active 9-(2-ethoxy-phenyl-hydrazono)-6-methyl-4-oxo-6,7,8,9-tetrahydro-4H-pyrido(1,2-a) pyrimidine-3-carboxylic acid as defined in claim 1.

21. Racemic or optically active 9-(3-ethoxy-phenyl-hydrazono)-6-methyl-4-oxo-6,7,8,9-tetrahydro-4H-pyrido(1,2-a)pyrimidine-3-carboxylic acid as defined in claim 1.

22. Racemic or optically active 9-(2-carboxy-phenyl-hydrazono)6-methyl-4-oxo-6,7,8,9-tetrahydro-4H-pyrido(1,2-a)pyrimidine-3-carboxylic acid as defined in claim 1.

23. A method of treating asthma in an animal subject comprising administering to said subject an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,461,769

DATED : July 24, 1984

INVENTOR(S) : Istvan Hermecz, et al.

It is certified that error appears in the above-identified patent and that said Letters Patent is hereby corrected as shown below:

ON THE TITLE PAGE INSERT:

— *The term of this patent subsequent to November 18, 1997, has been disclaimed. —.

Signed and Sealed this

Twenty-second Day of December, 1987

Attest:

DONALD J. QUIGG

Attesting Officer

Commissioner of Patents and Trademarks